US009701756B2

(12) United States Patent
Thie et al.

(10) Patent No.: US 9,701,756 B2
(45) Date of Patent: Jul. 11, 2017

(54) HUMANIZED ANTIBODY OR FRAGMENT THEREOF SPECIFIC FOR CD45R0

(71) Applicant: Miltenyi Biotec GmbH, Bergisch Gladbach (DE)

(72) Inventors: Holger Thie, Biberach (DE); Stefan Tomiuk, Cologne (DE); Iris Bürger, Rösrath (DE); Volker Nolle, Kurten (DE)

(73) Assignee: Miltenyi Biotec GmbH, Bergisch Gladbach (DE)

( * ) Notice: Subject to any disclaimer, the term of this patent is extended or adjusted under 35 U.S.C. 154(b) by 0 days.

(21) Appl. No.: 14/952,726

(22) Filed: Nov. 25, 2015

(65) Prior Publication Data
US 2016/0152733 A1    Jun. 2, 2016

(30) Foreign Application Priority Data
Nov. 26, 2014 (EP) ..................... 14194847

(51) Int. Cl.
*A61K 39/395* (2006.01)
*C07K 16/40* (2006.01)
*C07K 16/32* (2006.01)
*C07K 16/28* (2006.01)

(52) U.S. Cl.
CPC ............ *C07K 16/32* (2013.01); *C07K 16/289* (2013.01); *C07K 2317/24* (2013.01); *C07K 2317/55* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| 8,293,235 | B2 | 10/2012 | Borras et al. | |
| 2004/0110226 | A1* | 6/2004 | Lazar | C07K 16/00 435/7.1 |
| 2009/0196870 | A1* | 8/2009 | Ledbetter | C07K 16/2818 424/133.1 |
| 2012/0058906 | A1* | 3/2012 | Smider | C07K 16/00 506/9 |

FOREIGN PATENT DOCUMENTS

| EP | 1 421 191 B1 | 9/2011 |
| WO | WO-02/072832 A2 | 9/2002 |

OTHER PUBLICATIONS

Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Ahmad, Z.A. et al. (2012). "scFv Antibody: Principles and Clinical Application," *Clin. Dev. Immunol.* 980250:1-15.
Ahmadzadeh, V. et al. (2014, e-pub. Aug. 1, 2014). "Design, Expression and Characterization of a Single Chain Anti-CD20 Antibody; A Germline Humanized Antibody Derived From Rituximab," *Protein Expression and Purification* 102:45-51.
Altschul, S.F. et al. (1990). "Basic Local Alignment Search Tool," *J. Mol. Biol.* 215:403-410.
Carter, P. et al. (May 1992). "Humanization of an Anti-p185$^{HER2}$ Antibody for Human Cancer Therapy," *Proc. Natl. Acad. Sci. USA* 89:4285-4289.
Carter, P. et al. (Feb. 1992). "High Level *Escherichia coli* Expression and Production of a Bivalent Humanized Antibody Fragment," *Bio/Technology* 10:163-167.
Conchillo-Sole, O. et al. (Feb. 27, 2007). "AGGRESCAN : A Server for the Prediction and Evaluation of "Hot Spots" of Aggression in Polypeptides," *BMC Bioinformatics* 8(65):1-17.
Giudicelli, V. et al. (2005). "IMGT/GENE-DB: A Comprehensive Database for Human and Mouse Immunoglobulin and T Cell Receptor Genes," *Nucleic Acids Res.* 33:D256-D261.
Kolbinger, F. et al. (1993). "Humanization of a Mouse Anti-Human IgE Antibody: Apotential Therapeutic for IgE-Mediated Allergies," *Protein Eng.* 6(8):971-980.
Lund, J. et al. (Oct. 15, 1991). "Human FcγRI and FcγRII Interact with Distinct but Overlapping Sites on Human IgG," *J. Immunol.* 147(8):2657-2662.
Maurer-Stroh, S. et al. (Mar. 2010). "Exploring the Sequence Determinants of Amyloid Structure Using Position-Specific Scoring Matrices," *Nature Methods* 7(3):237-242.
Morgan, A. et al. (1995). "The N Terminal End of the $C_H2$ Domain of Chimeric Human IgG1 Anti-HLA-DR is Necessary for C1q, FcγRI and FcγRIII Binding," *Immunology* 86:319-324.
Pearson, W.R. et al. (Apr. 1988). "Improved Tools for Biological Sequence Comparison," *Proc. Natl. Acad. Sci. USA* 85:2444-2448.
Pulido, R. et al. (Mar. 1994). "Identification of Amino Acids at the Junction of Exons 3 and 7 That are used for the Generation of Glycosylation-Related Human CD45RO and CD45RO-Like Antigen Specificities," *J. Exp. Med.* 179:1035-1040.
Riechmann, L. et al. (Mar. 24, 1988). "Reshaping Human Antibodies for Therapy," *Nature* 332:323-327.
Safdari, Y. et al. (2013). "Antibody Humanization Methods—A Review and Update," *Biotechnology and Genetic Engineering Reviews* 29(2):175-186.
Sato, K. et al. (1994). "Humanization of a Mouse Anti-Human Interleukin-6 Receptor Antibody Comparing Tow Methods for Selecting Huamn Framework Regions," *Mol Immunol.* 31(5):371-381.
Shalaby, M.R. et al. (Jan. 1992). "Development of Humanized Bispecific Antibodies Reactive with Cytotoxic Lymphocytes and Tumor Cells Overexpressing the HER2 Protooncogene," *J. Exp. Med.* 175:217-225.

(Continued)

Primary Examiner — Phillip Gambel
(74) Attorney, Agent, or Firm — Morrison & Foerster LLP

(57) ABSTRACT

The present invention provides a humanized antibody or fragment thereof specific for the antigen CD45R0, wherein said antibody or fragment thereof comprises a humanized heavy chain variable domain comprising a CDR1 region of SEQ ID NO:1, a CDR2 region of SEQ ID NO:2, and a CDR3 region of SEQ ID NO:3, and a humanized light chain variable domain comprising a CDR1 region of SEQ ID NO:4, a CDR2 region of SEQ ID NO:5, and a CDR3 region of SEQ ID NO:6. It is also provided the use of the present antibody or fragment thereof for enrichment or depletion of CD45R0-expressing cells from a sample comprising CD45R0-expressing cells.

4 Claims, 11 Drawing Sheets

(56) References Cited

OTHER PUBLICATIONS

Smith, S.H. et al. (1986). "Functional Subsets of Human Helper-Inducer Cells Defined by a New Monoclonal Antibody, UCHL1," *Immunology* 58: 63-70.

Smith, T.F. et al. (1981). "Identification of Common Molecular Subsequences," *J. Mol. Biol*.147:195-197.

Terry, L.A. et al. (1988). "The Monoclonal Antibody, UCHL1, Recongnizes a 180,000 MW Component of the Human Leucocyte-Common Anigen, CD45," *Immunol*. 64:331-336.

Valentine, M. et al. (2013, e-pub. Sep. 4, 2013). "Expression of the memory Marker CD450RO on Helper T Cells in Macaques," *PLoS ONE* 8(9)(e73969)1-16.

Walsh, I. et al. (2014, E-pub. May 21, 2014). "PASTA 2.0: An lmporved Server for Protein Aggregation Prediction," *Nucleic Acids Res*. 12:W301-W307.

Willuda, J. et al. (Nov. 15, 1999). "High Termal Stability Is Essential for Tumor Targeting of Antibody Fragments: Engineering of a Humanized Anti-Epithelial Glycoprotein-2 (Epithelial Cell Adhesion Molecule) Single-Chain Fv Fragment," *Cancer Res*. 59, 5758-5767.

\* cited by examiner

```
HC_muCD45R0      QITLKESGPGILQPSQTLSLTCSFSGFSLTTYGIGVGWIRQPPGKGLEWLTHIWWNDNKY
                                                  xxxxxxxxx                    xxxxxxxx
gr_IGHV2-5*01    QITLKESGPTLVKPTQTLTLTCTFSGFSLTTYGIGVGWIRQPPGKALEWLALIWWNDNKR HC_muCD45R0      YNTALRSRLTISKDSSNNQVLLKIANVDTADTATYYC
gr_IGHV2-5*01    YSPSLKSRLTITKDTSKNQVVLTMTNMDPVDTATYYC
```

FIG. 3

```
LC_muCD45R0      DVVMTQTPLSLPVSLGDQASISCRSSQSLLYSNGNTYLHWYLQKPGQSPKLLIYKLSNRF
                                              xxxxxxxxxx                        xxx
gr_IGKV2-30*01   DVVMTQSPLSLPVTLGQPASISCRSSQSLLYSNGNTYLNWFQQRPGQSPRRLIYKLSNRD LC_muCD45R0      SGVPDRFSGSGSGTDFTLKISRVEAEDLGVYFC
gr_IGKV2-30*01   SGVPDRFSGSGSGTDFTLKISRVEAEDVGVYYC
```

FIG. 4

```
gr_IGHV2-5*01  QITLKESGPTLVKPTQTLTLTCTFSGFSLTTYGIGVGWIRQPPGKALEWLALIWWNDNKR
               :::::::::::::::::::::::::::::::::::::::::::::::::xxxxxxxxx:xxxxxxx
HC_final       QITLKESGPTLVKPTQTLTLTCTFSGFSLTTYGIGVGWIRQPPGKALEWLTHIWWNDNKY gr_IGHV2-5*01  YSPSLKSRLTITKDTSKNQVVLTMTNMDPVDTATYYC
               ::::::::::::::xxxxx::::::::::::::::::
HC_final       YSPSLKSRLTITKDSSKNQVVLTMTNMDPVDTATYYCLYGYTYWGQGTLVTVSA
```

FIG. 5

```
gr_IGKV2-30*01  DVVMTQSPLSLPVTLGQPASISCRSSQSLLYSNGNTYLNWFQQRPGQSPRRLIYKLSNRD
                ::::::xxxxxxxxxxx:::::::::::::::::::::::::::::::::::::::xxx
LC_final        DVVMTQTPLSLPVTLGQPASISCRSSQSLLYSNGNTYLHWYQQRPGQSPRRLIYKLSNRF gr_IGKV2-30*01  SGVPDRFSGSGSGTDFTLKISRVEAEDVGVYYC
                :::::::::::::::::::::::::::::::::xxxxxxxxxx
LC_final        SGVPDRFSGSGSGTDFTLKISRVEAEDVGVYYCSQSTHVPWTFGGGTKLEIK
```

FIG. 13A

```
      |_____FR1_____|   |__CDR1__|   |____FR2____|   |__CDR2__|
1........10...15_16.....23_26_27........38_3941..46_47.......55_56......65_66..
|       |           |   |       |       |   |       |         |       |   |
|       |           |   |       |       |   |       |         |       |   |
QITLKESGP.GILQP SQTLSLTCSFS GFSLT..TYGIG VGWIRQPP GKGLEWLTH IWW...NDNK YYNT

|_____FR3_____|           |___CDR3___|   |__FR4__|
...74_75......84_85.89......96_97....104_105.111112117_118.....128
|       |           |        |   |             |       |
|       |           |        |   |             |       |
ALR.S RLTISKDSSN NQVLLKIANVDT ADTATYYC LYG........YTY WGQGTLVTVSA
```

FIG. 13B

```
      |_____FR1_____|   |__CDR1__|   |____FR2____|   |__CDR2__|
1........10...15_16.....23_26_27........38_3941..46_47.......55_56......65_66..
|       |           |   |       |       |   |       |         |       |   |
|       |           |   |       |       |   |       |         |       |   |
DVVMTQTPLSLPVSL GDQASISCRSS QSLLYS.NGNTY LHWYLQKP GQSPKLLIY KL........S NRFS

|_____FR3_____|           |___CDR3___|   |__FR4__|
...74_75......84_85.89......96_97....104_105.111112117_118.....128
|       |           |        |   |             |       |
|       |           |        |   |             |       |
GVP.D RFSGSG..SG TDFTLKISRVEA EDLGVYFC SQSTH....VPWT FGGGTKLEIK.
```

FIG. 14A

```
         |_____FR1_____|  |_CDR1_|  |_____FR2_____|  |_CDR2_|
1........10...15_16.....23.26_27.........38_3941..46_47......55_56......65_66..
|........|....|.|.......|..|.|..........|..|.|...|..|.|......|..|.......|..|..
EVQLVESGG.GLVQP GGSLRLSCAAS GFNI....KDTY IHWVRQAP GKGLEWVAR IYPT..NGYT RYAD

|_____FR3_____|  |___CDR3___|  |___FR4___|
...74_75......84_85..89......96_97...104_105.111112117_118.....128
...|..|.......|..|...|.......|..|....|...|...|..|..|..|...|....|
SVK.G RFTISADTSK NTAYLQMNSLRA EDTAVYYC SRWGGDGFYAMDY WGQGTLVTVSS
```

FIG. 14B

```
         |_____FR1_____|  |_CDR1_|  |_____FR2_____|  |_CDR2_|
1........10...15_16.....23.26_27.........38_3941..46_47......55_56......65_66..
|........|....|.|.......|..|.|..........|..|.|...|..|.|......|..|.......|..|..
DIQMTQSPSSLSASV GDRVTITCRAS QDV.......NTA VAWYQQKP GKAPKLLIY SA........S FLYS

|_____FR3_____|  |___CDR3___|  |___FR4___|
...74_75......84_85..89......96_97...104_105.111112117_118.....128
...|..|.......|..|...|.......|..|....|...|...|..|..|..|...|....|
GVP.S RFSGSR..SG TDFTLTISSLQP EDFATYYC QQHYT...TPPT FGQGTKVEIK.
```

HUMANIZED ANTIBODY OR FRAGMENT THEREOF SPECIFIC FOR CD45R0

CROSS REFERENCE TO RELATED APPLICATIONS

This application claims priority to European Application No. EP14194847.1 filed Nov. 26, 2014, incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 212302003000SeqList.txt, date recorded: Nov. 24, 2015, size: 35 KB).

FIELD OF INVENTION

The present invention relates to the field of humanized antibodies or fragments thereof, in particular to antibodies or fragments thereof specific for the antigen CD45R0.

BACKGROUND OF THE INVENTION

The receptor-type tyrosine-protein phosphatase C, also known as PTPRC, is an enzyme that, in humans, is encoded by the PTPRC gene. PTPRC is also known as CD45 antigen (SEQ ID NO:29). The family of protein tyrosine phosphatases are known to be signaling molecules that regulate a variety of cellular processes including cell growth, differentiation, mitotic cycle, and oncogenic transformation. PTPRC (CD45 antigen) contains an extracellular domain including two fibronectin type-III domains, a single transmembrane segment and a cytoplasmic domain with two tyrosine-protein phosphatase domains. The first phosphatase domain has enzymatic activity, while the second one seems to affect the substrate specificity of the first one. PTPRC (CD45 antigen) is heavily N- and O-glycosylated, having 19 published N-glycosylation sites (UniProt entry P08575, see world wide web at uniprot.org). PTPRC (CD45 antigen) is expressed in leukocytes. CD45R0 (sometimes also written as CD45RO) is a splice variant or isoform of CD45 antigen, which has a shortened extracellular domain containing mainly the fibronectin type-III domains due to removal of exons 4-6 (which encode RA, RB and RC). Other splice variants or isoforms comprise CD45RA, CD45RB, CD45RC, CD45RAB, CD45RAC, CD45RBC, and CD45R (ABC). CD45R0 is expressed in subsets of T-cells such as activated and memory T-cells, in subsets of B-cells, monocytes, macrophages, and in subsets of natural killer cells in patients with an NK lymphocytosis. CD45RA is expressed in B-cells, naïve T-cells, and monocytes. CD45RB is expressed in subsets of T-cells, B-cells, monocytes, macrophages, and granulocytes. Due to the many different isoforms, the high degree of glycosylation and the short extracellular domain of CD45R0 antigen, it is complicated to generate functionally active and specific antibodies and fragments thereof against CD45R0. The murine antibody clone UCHL1 (Smith et al. (1986) Immunology 58, 63-70) is the most commonly used functional antibody against the human cell surface antigen CD45R0. The exact epitope on CD45R0 to which UCHL1 binds remains unclear, but it is destroyed by treatment with either neuraminidase or O-glycosidase (Pulido et al. (1994) J Exp Med 179, 1035-1040).

Antibodies against CD45R0 can be used for positive selection/enrichment or depletion of CD45R0-positive cells. Humanized antibodies or fragments thereof are useful for clinical and cell therapeutic purposes as they are less immunogenic when administered to human patients compared to non-humanized antibodies or fragments thereof such as murine antibodies or fragments thereof. Techniques for humanization of non-human antibodies are known-in-the-art and comprise complementary determining regions (CDR) grafting into a human or humanized framework, wherein the grafted CDRs are typically derived from a rodent antibody. CDRs are part of the variable regions in antibodies or fragments thereof, where these molecules bind to their specific antigen. They are embedded into framework regions which are much less variable than the CDRs.

There are several approaches to select an appropriate framework. In one approach, a well-known and field-tested framework can be used which already has been shown to generate functional antibodies and fragments thereof which can be expressed at high level. In another approach, a human framework sequence is selected from a group of germline sequences which shows a high degree of identity to the original framework amino acid sequence ("germline humanization"; Ahmadzadeh et al. (2014), Protein Expression and Purification 102, 45-51). In some cases, the CDR sequences are additionally included to the framework sequence for the selection of a human framework with a high degree of identity. Depending on the amino acid sequence of the antibody to be humanized, the highest degree of identity of a germline framework sequence to the original framework sequence may be as low as 50% for the heavy chain variable domain and 40% for the light chain variable domain. Depending on the exact sequence used for the determination of the germline framework sequence with highest identity, for example including or excluding the CDR regions, the resulting sequences may differ from each other, meaning that more than one framework sequence may exist that per definition has the highest degree of identity to the original framework amino acid sequence.

Compared with framework regions derived from mature IgGs, the germline genes have less intraclonal somatic hypermutations. Therefore, it is expected that humanized antibodies derived from germline frameworks show lower immunogenicity than humanized antibodies with mature IgG frameworks.

In many cases, the affinity of antibodies engineered by CDR grafting is significantly reduced. Some rodent residues in framework regions, referred to as Vernier zone residues, have been demonstrated to affect the conformation of CDR loops and affinity of antibodies. These residues are located in the beta-sheet framework regions closely underlying the CDRs. Therefore, after the selection of desired human frameworks these residues are preferably maintained in humanized antibodies (Safdari et al. (2013) Biotechnology and Genetic Engineering Reviews 29, 175-186). The change of a human Vernier zone residue back to the original rodent residue at the respective position within the antibody variable regions is referred to as a "backmutation". Techniques for backmutations and the selection of amino acid residues to be backmutated are known-in-the-art and comprise structure-based approaches as well as random mutagenesis.

EP1421191 discloses humanized antibodies against CD45 antigen isoforms. The described antibody binds to CD45R0 and to CD45RB, whereas antibody clone UCHL1 specifically binds CD45R0. The specific binding of UCHL1 was published by Terry et al. (1988) Immunol. 64, 331-336, showing that antibodies such as UCHL1 selectively bind to the 180 kDa isoform CD45R0 (without any of the variable exons A, B or C) which appears to be restricted to a subset of activated T cells, memory cells and cortical thymocytes and is not detected on B cells.

It does not seem to exist a humanized antibody or fragment thereof against CD45 which only binds to the CD45R0 isoform of the antigen. Therefore, there is a need in the art for a humanized antibody or fragment thereof specific for the CD45R0 isoform of the CD45 antigen which can be used for clinical and cell therapeutic purposes, for example as part of a clinical cell separation reagent.

All references cited herein, including patent applications and publications, are incorporated by reference in their entirety.

SUMMARY OF THE INVENTION

As it was the aim to develop a recombinant antibody or fragment thereof specific for the CD45R0 isoform of CD45 antigen for a clinical environment, the favorite protein expression system is a non-mammalian system due to lower regulatory requirements. Recombinant proteins derived from *E. coli* or yeast cells cannot be contaminated by human pathogenic viruses in contrast to proteins derived from mammalian cells. Further on, a humanization of the antibody or fragment thereof minimizes immunogenic reactions when administered directly or indirectly to human patients.

It was found that the expression level of the murine CD45R0 antibody clone UCHL1 as a Fab molecule in *E. coli* as well as in *Pichia Pastoris* was very low and about 10-fold lower than the average expression level of other recombinant Fabs such as CD3, CD8 and CD25. It was also found that expression of the murine CD45R0 antibody clone UCHL1 as a Fab molecule in the mammalian cell line HEK293 likewise resulted in a very low expression level compared to the full-length recombinant IgG. In silico aggregation analyses showed that CDR3 of the heavy chain is highly aggregation-prone and may cause the low expression level in several expression systems. Therefore, it was a surprising finding as disclosed herein that humanized antibodies of the clone UCHL1 or fragments thereof can be expressed in a non-mammalian system such as *E. coli* and *Pichia Pastoris* at all.

For humanization of the antibody or fragments thereof, the method of CDR grafting into a human or humanized framework was used. In one approach, an artificial framework derived from human consensus sequences was used, which essentially corresponds to the germline sequences IGVH 3-66 and IGVK 1-39 (IMGT® nomenclature, numbering system described by ImMunoGeneTics) and which was originally used for the humanization of the anti-c-erbB2 (anti-P185-Her2) monoclonal antibody 4d5 (Carter et al. (1992) Proc Natl Acad Sci USA 89, 4285-4289; Willuda et al. (1999) Cancer Res. 59, 5758-5767; the variable domains are described in SEQ ID NO:19 and SEQ ID NO:20). This artificial framework is designated herein as "4D5", the framework regions are described in FIG. 14. It was published that usage of the human consensus "4D5" as a framework for antibodies and fragments thereof often results in high expression levels, for example 1-2 g/L of soluble and functional anti-p185HER2 Fab' fragments expressed in *E. coli* (Carter et al. (1992) Biotechnology (N Y) 10, 163-167), and 400 mg/L of chimeric and humanized versions of anti-CD3 Fab' fragments expressed in *E. coli* (Shalaby et al. (1992) J. Exp. Med. 175, 217-225). It therefore could be expected that usage of "4D5" as a framework for the humanization of an antibody or fragment thereof often results in a high expression level and often in an increased expression level of the humanized antibody or fragment thereof compared to the non-humanized antibody or fragment thereof. The CDRs (according to IMGT® nomenclature) of CD45R0 antibody clone UCHL1 used for CDR grafting are described in SEQ ID NO:1, SEQ ID NO:2, and SEQ ID NO:3 for the heavy chain variable domain and in SEQ ID NO:4, SEQ ID NO:5, and SEQ ID NO:6 for the light chain variable domain (see FIG. 9A and FIG. 9B for the IMGT® nomenclature). The framework sequences comprise the framework regions (FR) FR1, FR2, FR3, and FR4 (according to IMGT® nomenclature). For CDR grafting, the CDR regions CDR1, CDR2, and CDR3 were embedded in the naturally occurring order into the framework sequence, resulting in an order of sequence FR1-CDR1-FR2-CDR2-FR3-CDR3-FR4. One resulting humanized sequence of CD45R0 antibody heavy and lights chains using the "4D5" framework is shown in SEQ ID NO:15 (heavy chain) and SEQ ID NO:16 (light chain).

In the second approach, a natural sequence, namely a human germline sequence with high identity to the murine CD45R0 antibody clone UCHL1 framework sequence was used as framework donor ("germline humanization").

For CDR grafting, again the CDR regions CDR1, CDR2, and CDR3 were embedded into the donor framework sequence in their naturally occurring order, resulting in an order of sequence FR1-CDR1-FR2-CDR2-FR3-CDR3-FR4. One resulting humanized sequence of CD45R0 antibody heavy and lights chains using a human germline sequence with high identity to CD45R0 antibody clone UCHL1 framework sequence is shown in SEQ ID NO:17 (heavy chain) and SEQ ID NO:18 (light chain).

Backmutations were introduced into the CDR-grafted sequences to minimize or prevent loss of affinity or even to increase affinity of the humanized CD45R0 antibody or fragment thereof to CD45R0. The introduction of backmutations at amino acid positions 1, 2, 25, 39, 40, 42, 53, 54, 55, 66, 72, 80, 82, and 87 of the heavy chain and at positions 2, 3, 7, 22, 25, 39, 40, 66, 67, 68, 74, and 80 of the light chain (according to the IMGT® nomenclature) into humanized UCHL1 antibodies or fragments thereof led to antibodies or fragments thereof which have a suitable affinity (or relative affinity) towards its cellular antigen CD45R0. Alternatively and more preferred, the introduction of backmutations at amino acid positions 54, 55, 66, and 82 of the heavy chain and at positions 7, 40, 42, 52, and 68 of the light chain (according to the IMGT® nomenclature) into humanized UCHL1 antibodies or fragments thereof led to antibodies or fragments thereof which also have a suitable affinity (or relative affinity) towards its cellular antigen CD45R0.

Following observations were made: Firstly and surprisingly, variants based on the "4D5" framework with different sets of backmutations (heavy chain: amino acid residues at positions 25, 39, 40, 42, 53, 54, 55, 66, 80, 82, 87 (SEQ ID NO:9), plus light chain: amino acid residues at positions 25, 39, 40, 66, 67, 68 (SEQ ID NO:10); or heavy chain: amino acid residues at positions 1, 2, 25, 39, 40, 42, 53, 54, 55, 66, 72, 80, 82, 87 (SEQ ID NO:11), plus light chain: amino acid residues at positions 2, 3, 7, 22, 25, 39, 40, 66, 67, 68, 74, 80 (SEQ ID NO:12), respectively) can be expressed in a prokaryotic system, however with levels lower than compared to the parental murine CD45R0 antibody clone UCHL1 sequence (SEQ ID NO:13 and SEQ ID NO:14). Secondly and more surprisingly, the use of a human germline framework sequence with high sequence identity to the UCHL1 sequence (IGHV2-5*01 and IGKV2-30*01, respectively) instead of the "4D5" framework in combination with backmutations (heavy chain: amino acid residues at positions 54, 55, 66, 82 (SEQ ID NO:7); light chain: amino acid residues at positions 7, 40, 42, 52, 68 (SEQ ID NO:8)) resulted in an unexpected 3-fold higher expression level of this humanized CD45R0 antibody variant compared to the parental murine CD45R0 antibody UCHL1 sequence. This was also surprising because all variants are having the same CDR3 sequence in their heavy chain which is predicted to be prone to aggregate. Thirdly and surprisingly, the use of a human germline framework sequence with high sequence identity to the UCHL1 sequence (IGHV2-5*01 and IGKV2-30*01, respectively) in combination with backmutations (heavy chain: amino acid residues at positions 54, 55, 66, 82 (SEQ ID NO:7); light chain: amino acid residues at positions 7, 40, 42, 52, 68 (SEQ ID NO:8)) resulted in an unexpected higher relative affinity of this humanized CD45R0 antibody variant compared to the parental murine CD45R0 antibody UCHL1 sequence towards cell-bound CD45R0 antigen.

Therefore, the invention comprises a humanized antibody or fragment thereof specific for the antigen CD45R0, wherein said antibody or fragment thereof comprises a humanized heavy chain variable domain comprising a CDR1 region of SEQ ID NO:1, a CDR2 region of SEQ ID NO:2, and a CDR3 region of SEQ ID NO:3, and a humanized light chain variable domain comprising a CDR1 region of SEQ ID NO:4, a CDR2 region of SEQ ID NO:5, and a CDR3 region of SEQ ID NO:6. Different embodiments of said humanized antibody or fragment thereof are disclosed herein.

The invention also comprises isolated polynucleotides encoding for said antibody or fragment thereof, an expressing vector comprising said polynucleotides, an expressing system comprising said polynucleotides and a host cell expressing said antibody or fragment thereof, a host cell comprising said polynucleotides, and the use of said antibody or fragment thereof for enrichment or depletion of CD45R0-expressing cells from a sample comprising CD45R0-expressing cells.

BRIEF DESCRIPTION OF THE DRAWINGS

FIG. 1A and FIG. 1B show in silico aggregation analysis of parental murine CD45R0 antibody clone UCHL1 heavy chain (FIG. 1A, SEQ ID NO:13) and light chain (FIG. 1B, SEQ ID NO:14) variable domains. For each amino acid residue, a numerical score was calculated using standard software known in the art which predicts the tendency of protein aggregation. Higher scores stand for higher aggregation tendency. The minimum score is 0 (not aggregation-prone) and the maximum score is 100 (highly aggregation-prone).

FIG. 2 shows a sequence alignment of FR1, CDR1, FR2, CDR2, and FR3 of the heavy chain variable domain of the parental murine CD45R0 antibody clone UCHL1 ("HC_muCD45R0", SEQ ID NO:31) and the amino acid sequence encoded by the allele IGHV2-5*01 of the human germline V gene segment after substitution of its CDR regions by the CDR regions of the parental CD45R0 antibody clone UCHL1 ("gr_IGHV2-5*01", SEQ ID NO:27). CDR regions according to the IMGT® definition are labeled by "x", amino acid residues identical between the two sequences are indicated by ":".

FIG. 3 shows a sequence alignment of FR1, CDR1, FR2, CDR2, and FR3 of the light chain variable domain of the parental murine CD45R0 antibody clone UCHL1 ("LC_muCD45R0", SEQ ID NO:32) and the amino acid sequence encoded by the allele IGKV2-30*01 of the human germline V gene segment after substitution of its CDR regions by the CDR regions of the parental CD45R0 antibody clone UCHL1 ("gr_IGKV2-30*01", SEQ ID NO:28). Legend as in FIG. 2.

FIG. 4 shows a sequence alignment of FR1, CDR1, FR2, CDR2, and FR3 of the heavy chain variable domain encoded by the allele IGHV2-5*01 of the human germline V gene segment after substitution of its CDR regions by the CDR regions of the parental CD45R0 antibody clone UCHL1 ("gr_IGHV2-5*01", SEQ ID NO:27) and the final humanized sequence of the heavy chain variable domain of the CD45R0 antibody including backmutations, CDR3 and FR4 ("HC_final", SEQ ID NO:7). CDR regions according to the IMGT® definition are labeled by "x", amino acid residues identical between the two sequences are indicated by ":".

FIG. 5 shows a sequence alignment of FR1, CDR1, FR2, CDR2, and FR3 of the light chain variable domain encoded by the allele IGKV2-30*01 of the human germline V gene segment after substitution of its CDR regions by the CDR regions of the parental CD45R0 antibody clone UCHL1 ("gr_IGKV2-30*01", SEQ ID NO:28) and the final humanized sequence of the light chain variable domain of the CD45R0 antibody including backmutations, CDR3 and FR4 ("LC_final", SEQ ID NO:8). Legend as in FIG. 4.

FIG. 10A: Fab variants "muCD45R0" and "huCD45R0_v3" were used. In addition, a CD45RA-FITC staining was applied to discriminate CD45R0-positive cells. The fluorescence intensity of anti-His-PE is plotted against the fluorescence intensity of CD45RA-FITC. FIG. 10B: Fab variants "muCD45R0", "huCD45R0_v2", and "huCD45R0_v3" were used. The median fluorescence of anti-His-PE is plotted for each Fab variant.

FIG. 13A and FIG. 13B show numbering system and definitions of framework and CDR regions according to the IMGT® nomenclature using heavy chain variable region (FIG. 13A, SEQ ID NO:13) and light chain variable region (FIG. 13B, SEQ ID NO:14) of CD45R0 antibody clone UCHL1 as example. Positions which are not occupied by an amino acid residue in the antibody sequence are marked with a dot within the sequences. FR1, FR2, FR3, FR4, framework regions 1-4; CDR1, CDR2, CDR3, complementarity determining regions 1-3.

FIG. 14A and FIG. 14B show numbering system and definitions of framework and CDR regions according to the IMGT® nomenclature of humanized anti-P185-Her2 antibody 4d5 heavy chain (FIG. 14A, SEQ ID NO:19) and light chain (FIG. 14B, SEQ ID NO:20). Positions which are not occupied by an amino acid residue in the humanized anti-P185-Her2 antibody 4d5 sequences are marked with a dot within the sequences. FR1, FR2, FR3, FR4, framework regions 1-4; CDR1, CDR2, CDR3, complementarity determining regions 1-3.

DETAILED DESCRIPTION OF THE INVENTION

Figure 6:
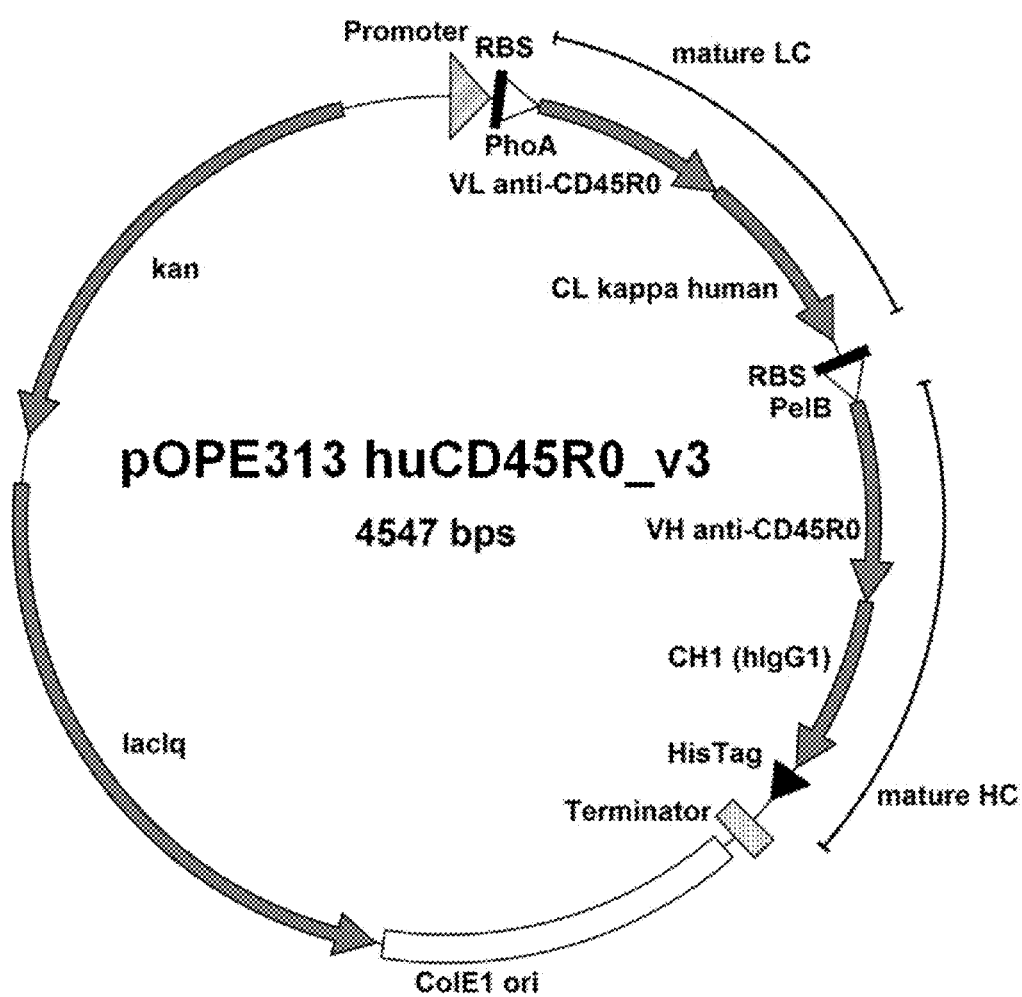
FIG. 6 is a plasmid map of the prokaroytic vector for the expression of Fab fragments against CD45R0 antigen in *E. coli*. LC, light chain; HC heavy chain; VL, light chain variable domain; VH, heavy chain variable domain; CL light chain constant domain; CH1 (hIgG1), CH1 domain of human IgG1; RBS, ribosome binding site; His Tag, polyhistidine tag; kan, kanamycin resistance gene; lacIq, lac repressor gene; ori, origin of replication; PhoA, signal peptide PhoA; PelB, signal peptide PelB.

In a first aspect the invention provides a humanized antibody or fragment thereof specific for the antigen CD45R0, wherein said antibody or fragment thereof comprises a humanized heavy chain variable domain comprising a CDR1 region of SEQ ID NO:1, a CDR2 region of SEQ ID NO:2, and a CDR3 region of SEQ ID NO:3, and a humanized light chain variable domain comprising a CDR1 region of SEQ ID NO:4, a CDR2 region of SEQ ID NO:5, and a CDR3 region of SEQ ID NO:6.

Said CDRs may be embedded into a framework sequence comprising the regions FR1, FR2, FR3, and FR4. The order of sequence may be FR1-CDR1-FR2-CDR2-FR3-CDR3-FR4.

Therefore, said humanized antibody or fragment thereof may comprise framework regions FR1, FR2, FR3, and FR4 of said humanized heavy chain variable domain, wherein said framework regions may be selected from the group consisting of artificial and natural sequences known-in-the-art for humanization of antibodies, and said humanized antibody or fragment thereof may comprise framework regions FR1, FR2, FR3, and FR4 of said humanized light chain variable domain, wherein said framework regions FR1, FR2, FR3, and FR4 of said humanized light chain variable domain may be selected from the group consisting of artificial and natural sequences known-in-the-art for humanization of antibodies.

Said artificial framework regions may be selected from the group consisting of "4D5", "FW 1.4" (as described in U.S. Pat. No. 8,293,235), "consensus VH SGI VL kIII" (as described in Kolbinger et al. (1993) Protein Eng. 6, 971-980), and "VH SGI consensus" (as described in Sato et al. (1994) Mol Immunol. 31, 371-381). Preferentially, the artificial framework region may be "4D5".

Therefore, the humanized heavy chain variable domain of said humanized antibody or fragment thereof may comprise artificial framework regions FR1, FR2, FR3, and FR4, wherein said artificial framework regions FR1, FR2, FR3, and FR4 are sequences having an identity of at least 70%, more preferentially at least 80%, most preferentially at least 90% to the "4D5" heavy chain variable sequence framework regions FR1, FR2, FR3, and FR4. The humanized light chain variable domain of said humanized antibody or fragment thereof may comprise artificial framework regions FR1, FR2, FR3, and FR4, wherein said artificial framework regions FR1, FR2, FR3 and FR4 are sequences having an identity of at least 70%, more preferentially at least 80%, most preferentially at least 90% to the "4D5" light chain variable sequence framework regions FR1, FR2, FR3, and FR4.

The framework regions of said humanized heavy chain variable domain and said light chain variable domain may comprise amino acid substitutions (backmutations) to increase the affinity of the antibody or fragment thereof compared to the humanized variant without backmutation.

Such backmutations may comprise within the heavy chain variable domain amino acid F at position 25, V at position 39, G at position 40, I at position 42, L at position 53, T at position 54, H at position 55, Y at position 66, K at position 80, S at position 82, and V at position 87, and within the light chain variable domain amino acid S at position 25, L at position 39, H at position 40, N at position 66, R at position 67, and F at position 68 according to the IMGT® nomenclature.

Preferentially, said humanized heavy chain variable domain comprises the amino acid sequence of SEQ ID NO:9 and said humanized light chain variable domain comprises the amino acid sequence of SEQ ID NO:10.

More preferred, such backmutations may comprise within the heavy chain variable domain amino acid Q at position 1, I at position 2, F at position 25, V at position 39, G at position 40, I at position 42, L at position 53, T at position 54, H at position 55, Y at position 66, R at position 72, K at position 80, S at position 82, and V at position 87, and within the light chain variable domain amino acid V at position 2, V at position 3, T at position 7, S at position 22, S at position 25, L at position 39, H at position 40, N at position 66, R at position 67, F at position 68, D at position 74, and G at position 80 according to the IMGT® nomenclature.

Therefore preferentially, said humanized heavy chain variable domain comprises the amino acid sequence of SEQ ID NO:11 and said humanized light chain variable domain comprises the amino acid sequence of SEQ ID NO:12.

The humanized heavy chain variable domain of said humanized antibody or fragment thereof may comprise natural framework regions FR1, FR2, FR3, and FR4, wherein said natural framework regions FR1, FR2, and FR3 are amino acid sequences having an identity of at least 70%, more preferentially at least 80%, most preferentially at least 90% to the framework regions FR1, FR2, and FR3 encoded by one allele of the IGHV2-5 gene as provided within the IMGT® reference set of human variable heavy chain germline sequences. The humanized light chain variable domain of said humanized antibody or fragment thereof may comprise artificial framework regions FR1, FR2, FR3, and FR4, wherein said artificial framework regions FR1, FR2, and FR3 are amino acid sequences having an identity of at least 70%, more preferentially at least 80%, most preferentially at least 90% to the framework regions FR1, FR2, and FR3 encoded by one allele of the IGKV2-30 gene as provided within the IMGT® reference set of human variable light chain germline sequences.

Said natural framework regions may be selected from human germline sequences known in the art. Preferentially, said germline sequences may be selected from the group consisting of IGHV2-5, IGHV2-26, IGHV2-70, IGHV2-70D, and IGHV2-0R16-5 for the heavy chain variable domain and said germline sequences may be selected from the group consisting of IGKV2-24, IGKV2D-24, IGKV2D-26, IGKV2-28, IGKV2-29, IGKV2D-29, IGKV2-30, IGKV2D-30, and IGKV2-40 for the light chain variable domain.

Said framework regions of said humanized heavy chain variable domain and of said light chain variable domain may be selected from amino acid sequences encoded by human germline sequences with high identity to the framework regions of the parental non-human heavy and light chain variable domains. The CDR regions may be included for the determination of identity.

Said humanized framework regions of heavy chain variable domain and of light chain variable domain may be preferentially selected from framework regions encoded by one allele of the human IGHV2-5 gene for the humanized heavy chain variable domain, and selected from framework regions encoded by one allele of the human IGKV2-30 gene for the humanized light chain variable domain. The gene IGHV2-5 comprises the alleles IGHV2-5*01, IGHV2-5*02, IGHV2-5*03, IGHV2-5*04, IGHV2-5*05, IGHV2-5*06, IGHV2-5*08, and IGHV2-5*09. The gene IGKV2-30 comprises the alleles IGKV2-30*01 and IGKV2-30*02.

More preferentially, said humanized antibody or fragment thereof comprises natural framework regions FR1, FR2, and FR3 of said humanized heavy chain variable domain which are amino acid sequences having an identity of at least 70%, more preferentially at least 80%, most preferentially at least 90% to the framework regions FR1, FR2, and FR3 encoded by one allele of the IGHV2-5 gene, and said humanized antibody or fragment thereof comprises natural framework regions FR1, FR2, and FR3 of said humanized light chain variable domain which are amino acid sequences having an identity of at least 70%, more preferentially at least 80%, most preferentially at least 90% to the framework regions FR1, FR2, and FR3 encoded by one allele of the IGKV2-30 gene.

Most preferentially, said humanized framework regions of heavy chain variable domain and of light chain variable domain are comprising framework regions encoded by the allelic variant IGHV2-5*01 of human germline sequences for the humanized heavy chain variable domain and framework regions encoded by the allelic variant IGKV2-30*01 of human germline sequences for the humanized light chain variable domain. Therefore, said humanized heavy chain variable domain may comprise the amino acid sequence of SEQ ID NO:17 and said humanized light chain variable domain comprises the amino acid sequence of SEQ ID NO:18.

Again, the framework region of said humanized heavy chain variable domain and said humanized light chain variable domain may contain amino acid substitutions (backmutations) to increase the affinity of the antibody or fragment thereof compared to the variant without backmutation.

Said antibody or fragment thereof may comprise a humanized heavy chain variable domain and a humanized light chain variable domain as disclosed herein wherein the heavy chain variable domain comprises amino acid T at position 54, H at position 55, Y at position 66, and S at position 82, and wherein the light chain variable domain comprises amino acid T at position 7, H at position 40, Y at position 42, L at position 52, and F at position 68 according to the IMGT nomenclature.

Therefore preferentially, said humanized heavy chain variable domain comprises the amino acid sequence of SEQ ID NO:7 and said humanized light chain variable domain comprises the amino acid sequence of SEQ ID NO:8.

In one aspect the invention provides isolated polynucleotides encoding for humanized antibodies or fragments thereof as disclosed herein.

In another aspect the invention provides an expression system comprising the polynucleotides encoding an antibody or fragment thereof as disclosed herein, and a host cell expressing said antibody or fragment thereof.

In a further aspect the invention provides a host cell comprising the polynucleotides encoding the antibodies or fragments thereof as disclosed herein.

In another aspect the invention provides the use of the antibody or fragment thereof according to the invention for enrichment or depletion of CD45R0-expressing cells from a sample comprising CD45R0-expressing cells.

Said use may comprise the generation of a therapeutic applicable cell composition.

Preferentially, the antibodies or fragments thereof of the invention bind specifically to CD45R0 with a relative affinity of at least 20%, 30%, 50%, 70%, 90%, 100%, or more than 100% for the CD45R0 antigen when compared to the parental murine CD45R0 antibody clone UCHL1.

DEFINITIONS

Unless defined otherwise, technical and scientific terms used herein have the same meaning as commonly understood by one of ordinary skill in the art to which this invention belongs.

The term "antibody" as used herein is used in the broadest sense to cover the various forms of antibody structures including but not being limited to monoclonal and polyclonal antibodies (including full length antibodies), multispecific antibodies (e.g. bispecific antibodies), antibody fragments, immunoadhesins and antibody-immunoadhesin chimeras, that specifically recognize (i.e. bind) a target antigen. The antibody according to the invention is preferably a humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include Fab (fragment antigen binding), scFv (single chain fragment variable), single domain antibodies, diabodies, dsFv, Fab', diabodies, single-chain antibody molecules, and multispecific antibodies formed from antibody fragments. scFv antibodies are, e.g., described in Ahmad et al. (2012) Clin Dev Immunol. 2012, 980250. The term "humanized antibody" refers to antibodies in which the framework and/or CDR have been modified to comprise the CDR of an immunoglobulin of different species as compared to that of the parent immunoglobulin. In a preferred embodiment, a rodent (e.g., mouse) CDR is grafted into the framework region of a human antibody to prepare the "humanized antibody" (an example is given in Riechmann et al. (1988) Nature 332, 323-327). A humanized antibody binds to the same or similar antigen as the donor antibody that provides the CDRs. The acceptor framework of a humanized immunoglobulin may have a limited number of substitutions by amino acids taken from the donor framework. Humanized molecules can have additional conservative amino acid substitutions which have substantially no effect on antigen binding or other immunoglobulin functions. Conservative substitutions generally maintain (a) the structure of the polypeptide backbone in the area of the substitution, for example, as a sheet or helical conformation, (b) the charge or hydrophobicity of the molecule at the target site, and/or (c) the bulk of the side chain.

As used herein, the terms "parent" and "parental" with regard to an antibody sequence refer to the antibody sequence that is to be humanized. A parental antibody therefore is the non-human antibody clone to be humanized, usually of a rodent origin. The murine antibody clone UCHL1 against CD45R0 of the present invention is an example of a parental antibody.

As used herein, the term "muCD45R0" refers to a chimeric antibody and fragment thereof against the human antigen CD45R0, comprising variable regions of the parental murine antibody and constant regions of human origin. Accordingly, the term "huCD45R0_vX" (wherein X represents a number of 1, 2, 3, 4, or 5) refers to a humanized antibody and fragment thereof against the human antigen CD45R0.

As used herein, the term "antigen" is intended to include substances that evoke the production of one or more antibodies. Each antibody binds to a specific antigen by way of an interaction similar to the fit between a lock and a key. The substance may be from the external environment or formed within the body. The term "antigen" comprises, but is not limited to, proteins, peptides, polypeptides, oligopeptides, lipids, carbohydrates, and combinations thereof, for example a glycosylated protein. An antigen may be on the cell surface or inside the cell. Preferentially, an antigen is on the cell surface of a cell. Preferentially, the CD45R0 antigen is a mammalian CD45R0 antigen. Most preferred, the CD45R0 antigen is a human CD45R0 antigen.

The terms "specifically binds to" or "specific for" with respect to an antigen-binding domain of an antibody or fragment thereof refer to an antigen-binding domain which recognizes and binds to a specific antigen, i.e. CD45R0, but does not substantially recognize or bind other antigens in a sample. An antigen-binding domain that binds specifically to an antigen from one species may bind also to that antigen from another species. This cross-species reactivity is not contrary to the definition of that antigen-binding domain as specific. An antigen-binding domain that specifically binds to the CD45R0 antigen may not bind substantially to different variants of the antigen (allelic variants, splice variants, isoforms etc., such as CD45RA or CD45RB). This cross reactivity is contrary to the definition of that antigen-binding domain as specific.

The term "domain" refers to a protein structure which retains its tertiary structure independently of the remainder of the protein. In some cases, domains have discrete functional properties and can be added, removed or transferred to another protein without a loss of function.

The term "affinity" refers to the strength of the sum total of non-covalent interactions between a single binding site of a molecule (e.g., binding arm of an antibody) and its binding partner (e.g., an antigen). Unless indicated otherwise, as used herein, "binding affinity" refers to intrinsic binding affinity which reflects an 1:1 interaction between members of a binding pair (e.g., antigen-binding protein and its antigen). The affinity of a molecule X for its partner Y can generally be represented by the equilibrium dissociation constant ($K_D$). Affinity can be measured by common methods known in the art. The term "relative affinity" refers to the relative comparison of binding affinities of two binding molecules (e.g., antibodies) to the same binding partner (e.g., an antigen) using a method that does not provide absolute values for binding affinities (e.g., Biacore™ measurement) but allows the qualitative evaluation of binding affinities using relative values. Such a method may be the measurement of the fluorescent signal of an antibody fluorochrome which is bound to the antigen and wherein the fluorochrome is bound directly or indirectly to the antibody.

The "variable domain" or "variable region" (variable domain of a light chain (VL), variable domain of a heavy chain (VH)) as used herein denotes each of the pair of light and heavy chain domains which are involved directly in binding of the antibody to the antigen. The term "variable domain" refers to both variable domains of immunoglobulin light chains of the kappa type and variable domains of immunoglobulin light chains of the lambda type.

The "constant domain" or "constant region" (constant domain of a light chain (CL), constant domain of a heavy chain (CH)) as used herein denotes the domains that comprise the CL domain (in the case of the light chain) and the CH1, Hinge, CH2, CH3 and/or CH4 domains (in the case of the heavy chain) of an antibody. The constant region of the heavy chain differs in antibodies of different isotypes. In recombinant antibodies or fragments thereof, CH1, Hinge, CH2, CH3 and CH4 domains and fragments thereof of different isotypes may be combined. CH1, Hinge, CH2, CH3 and CH4 domains may also be chosen from different species. In a humanized Fab fragment, the constant domain is preferentially a human constant domain, more preferentially human CL and human IgG1 CH1.

The variable light and heavy chain domains have the same general structure and each domain comprises four framework (FR) regions whose sequences are widely conserved, connected by three "hypervariable regions" (or complementary determining regions, CDRs). The light and heavy chain variable domains of an antibody comprise, from N- to C-terminus, the domains FR1, CDR1, FR2, CDR2, FR3, CDR3, and FR4. The CDRs in each chain are held in their three-dimensional structure by the framework regions and form together with the CDRs from the other chain the antigen binding site. The assignment of CDR and FR regions to the antibody sequence as used herein is determined according to the IMGT® definition (see world wide web at imgt.org), also referred to as FR-IMGT® and CDR-IMGT®. There are other definitions of FR and CDR regions according to, for example, Kabat and Chothia, which may result in slightly different assignments of amino acid positions at the conjunctions of FR and CDR regions and therefore in slightly different CDR lengths.

The antibody according to the invention may comprise an Fc part from human origin which is selected from the subclasses IgG1, IgG2, IgG3, and IgG4. Preferentially the Fc part from human origin is of the subclass IgG1 or IgG4. The Fc part may contain amino acid substitutions, insertions and deletions. For example, amino acid residues involved in Fc gamma receptor binding may be substituted with other amino acid residues to minimize or to abolish this interaction.\

The antibody according to the invention can be a fragment thereof. The antibody fragment may contain amino acid substitutions, insertions and deletions. For example, a polyhistidine tag sequence may be inserted or added to any Fab fragment chain which allows for purification using affinity chromatography and/or immunological detection using anti-histidine antibodies.

The antibody according to the invention is preferably characterized in that the constant domains are of human origin. Such constant domains are well known in the art and described, e.g. by Kabat. Numbering according to Kabat and Chothia can be accomplished using websites such as see world wide web at bioinf.org.uk/abysis/sequence_input/key_ annotation/key_annotation.html.

As used herein, the term "CD45 antigen" refers to the CD45 protein, also known as receptor-type tyrosine-protein phosphatase C and CD45R0 antigen. Accordingly, the term "CD45R0 antigen" refers to the splice variant/isoform CD45R0 of CD45 antigen that has a shortened extracellular domain containing mainly the fibronectin type-III domains due to removal of exons 4-6.

The terms "splice variants" and "isoforms" as used herein have an interchangeable meaning and describe naturally occurring forms of the same protein, which are generated for example by alternative splicing of the coding mRNA or may be produced from very closely related genes. Isoforms may also be caused by single-nucleotide polymorphisms, i.e. small genetic differences between alleles of the same gene.

As used herein, the term "IMGT® nomenclature" describes the numbering scheme of antibody sequences according to IMGT (IMMUNOGENETICS INFORMATION SYSTEM®, on the world wide web at imgt.org; Giudicelli et al. (2005) Nucleic Acids Res. 33, D256-D261). FIGS. 13A and 13B exemplarily show the IMGT® nomenclature for the heavy and light chain variable domains of a CD45R0 antibody.

As used herein, the term "IGKV" is used as abbreviation for immunoglobulin kappa variable region genes. The term "IGHV" is used as abbreviation for immunoglobulin heavy chain variable region genes.

As used herein, the term "CDR grafting" refers to a method of taking CDR regions of one antibody or fragment thereof and transferring these into the framework of a second antibody or fragment thereof wherein the receiving framework (acceptor framework) is not identical to the framework of the first antibody (donor framework).

As used herein, the terms "framework" and "framework regions" refer to the amino acid sequence of an antibody or fragment thereof comprising domains FR1, FR2, FR3, and FR4 of both heavy and light chain variable regions, i.e the variable domains without the CDR regions. Accordingly, the terms "germline framework" and "germline framework regions" refer to the variable antibody domains without the CDR regions encoded by human germline antibody genes.

As used herein, the term "natural sequence" refers to amino acid sequences which are known from nature (e.g. a sequence derived from a gene such as a germline gene, or a sequence of a naturally occurring antibody). Accordingly, the term "artificial sequence" refers to amino acid sequences which are not known from nature. Examples for an artificial sequence comprise a consensus sequence generated from two or more sequences, and a natural sequence modified by substitution, addition, or deletion of amino acids resulting in a sequence which is not known from nature. Methods for the generation of consensus sequences are known in the art.

As used herein, the term "germline humanization" refers to a method of selecting a human germline framework sequence which shows a high degree of identity to the parental antibody framework amino acid sequence, preferentially the highest identity. Starting with the amino acid sequence of the parental antibody, a search against a database of human germline sequences is conducted using software tools known to a person skilled in the art, for example "ssearch" (Smith and Waterman (1981) J. Mol Biol. 147, 195-197; Pearson and Lipman (1988) PNAS 85, 2444-2448) or "BLAST" (Altschul et al. (1990) J. Mol. Biol. 215, 403-410). The output of these software tools is usually a list of germline sequences ranked by a score and/or an E-value which are an indicator for the identity of listed germline sequences to the input sequence. Human germline sequences are available for example in the reference database IMGT® human IG reference directory (see world wide web at.imgt.org/vquest/refseqh.html). Depending on the differing definitions of CDR regions according to the different nomenclatures such as IMGT®, Kabat and Chothia and the exact procedure of selecting human germline framework sequences, there may be different germline framework sequences with show the highest identity to the original sequence. For example, excluding the CDR regions during "germline humanization" can result in a different sequence with highest identity than including CDR regions in the alignment.

As used herein, the term "identity" (of proteins and polypeptides) with respect to amino acid sequences is used for a comparison of proteins chains. Calculations of "sequence identity" between two sequences are performed as follows. The sequences are aligned for optimal comparison purposes (e.g., gaps can be introduced in one or both of a first and a second amino acid sequence for optimal alignment and non-homologous sequences can be disregarded for comparison purposes). The optimal alignment is determined as the best score using the "ssearch36" program in the FASTA36 software package (see world wide web at faculty.virginia.edu/wrpearson/fasta/) with a Blossum 50 scoring matrix with a gap-open penalty of −10, and a gap-extension penalty of −2. The amino acid residues at corresponding amino acid positions are then compared. When a position in the first sequence is occupied by the same amino acid residue at the corresponding position in the second sequence, then the molecules are identical at that position. The percent identity between the two sequences is a function of the number of identical positions shared by the sequences.

As used herein, the term "backmutation" refers to an amino acid substitution in the framework region of a humanized antibody sequence. This is usually done to increase the affinity of the antibody towards its antigen after humanization. Candidate residues for backmutation comprise, for example, positions with different amino acids in the humanized antibody after CDR grafting and the parental non-humanized antibody, and positions with different amino acids in the humanized antibody after CDR grafting and an antibody consensus sequence. Usually candidate residues are at sites of the framework regions that are important for the binding properties of the antibody and/or that determine the main chain conformations of the antigen binding loops.

Unlike in CDRs, more substantial changes in structure framework regions (FRs) can be made without adversely affecting the binding properties of an antibody. Changes to FRs include, but are not limited to, humanizing a nonhumanderived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J. Immunol. 147, 2657-2662; Morgan et al. (1995) Immunology 86, 319-324), or changing the species from which the constant region is derived.

As used herein, the term "Vernier zone residues" refers to amino acid residues in the antibody β-sheet framework underlying the CDRs which play a critical role in adjustment of the loop structures of the CDRs. Although these residues do not directly interact with the antigen, careful selection of these residues may prove essential for the success of loop transplants in antibodies, and variation of these sites may also have a role in shaping the diversity of structures found in the primary repertoire and a role in affinity maturation.

As used herein, the term "corresponding position" refers to the amino acid position at the same numbered position in a heavy chain variable domain or light chain variable domain sequence according to the IMGT® numbering system.

As used herein, the term "germline sequence" refers to an amino acid sequence encoded by unrearranged immunoglobulin V (variable), D (diversity) and/or J (joining) gene segments, or portions thereof, present in the genomic DNA of an organism. The framework regions FR1, FR2, and FR3 as well as the CDR regions CDR1 and CDR2 are encoded by the V gene segment, and framework region FR4 is encoded by the J gene segment. CDR3 of the heavy chain is assembled from a small part of a V gene segment, the whole D gene segment and a small part of a J gene segment. CDR3 of the light chain is assembled from a small part of a V gene segment and a small part of a J gene segment. During a process called V(D)J joining, additional nucleotides may be inserted at or deleted from the junctions, resulting in added or deleted amino acids within CDR3. For the identification of human germline sequences with high identity to the framework regions of the parental non-human heavy and light chain variable domains, the identity of framework regions FR1, FR2, and FR3 and optionally the CDR regions CDR1 and CDR2 may be used. Optionally, FR4 and CDR3 may also be used for the identification of human germline sequences with high identity.

The antibodies of the invention are typically recombinantly expressed polypeptides. The antibodies may be chimeric polypeptides, wherein the term "chimeric polypeptide" refers to an artificial (non-naturally occurring) polypeptide which is created by juxtaposition of two or more peptide fragments which do not otherwise occur contiguously.

As used herein, the terms "positive selection of cells" and "enrichment of cells" as used herein have an interchangeable meaning and refer to the isolation of a subpopulation of cells from a cell population including tissue. Methods suitable for the positive selection of cells comprise centrifugation, filtration, magnetic cell sorting and fluorescent cell sorting.

As used herein, the term "depletion of cells" as used herein refers to a process of negative selection that separates desired cells from undesired cells. Samples of cells as used herein may comprise cells of blood origin such as PBMC, of cell culture origin or of tissue origin such as brain or bone which may be dissociated before use. Methods suitable for the depletion of cells comprise centrifugation, filtration, magnetic cell sorting and fluorescent cell sorting.

The terms "CD45R0-expressing" and "CD45R0-positive" (CD45R0+) cells as used herein have an interchangeable meaning and describe cells which express the CD45R0 antigen. Accordingly, the terms "CD45R0 non-expressing" and "CD45R0-negative" (CD45R0−) cells as used herein have an interchangeable meaning and describe cells which do not express the CD45R0 antigen in a detectable manner.

The amino acid sequences of a CDR1 region, a CDR2 region and a CDR3 region of a humanized heavy chain variable domain, and the amino acid sequences of a CDR1 region, a CDR2 region and a CDR3 of a humanized light chain variable domain are given in SEQ ID NO:1, SEQ ID NO:2, SEQ ID NO:3, SEQ ID NO:4, SEQ ID NO:5 and SEQ ID NO:6, respectively (in the one-letter code of amino acids). The amino acid sequences of a heavy chain variable domain and a light chain variable domain are given in SEQ ID NO:7 and SEQ ID NO:8, respectively (in the one-letter code of amino acids).

The amino acid sequences as given in SEQ ID NO:7 to SEQ ID NO:12 and in SEQ ID NO:15 to SEQ ID NO:18 refer to all constellations of the respective amino acid sequence which retains the intended function of the respective amino acid sequence as defined herein. In other words, the divergences of SEQ ID NO:7 to SEQ ID NO:12 and SEQ ID NO:15 to SEQ ID NO:18, respectively, should not affect their potential as binding specifically to the antigen CD45R0. Therefore, the amino acid sequences of SEQ ID NO:7 to SEQ ID NO:12 and SEQ ID NO:15 to SEQ ID NO:18 can be the full length amino acid sequence of the SEQ ID NO:7 to SEQ ID NO:12 and SEQ ID NO:15 to SEQ ID NO:18, respectively. It can also be a variant thereof which have some amino acids deleted, added or replaced while still retaining the intended function as described herein. Therefore, included in this definition are variants of the amino acid sequences in SEQ ID NO:7 to SEQ ID NO:12 and SEQ ID NO:15 to SEQ ID NO:18, respectively. In the context of the present invention, "sequence identity" may be determined using pairwise alignments using alignments programs for amino acid sequences well known to the art.

The term "human germline sequences with high identity to the framework regions of the original non-human heavy and light chain variable domains" as used herein refers to amino acid sequences (encoded by germline genes) of human germline heavy and light chain variable framework domains FR1, FR2, and FR3 having a sequence identity of at least 40%, 50%, 60%, 70%, or 80% at the amino acid sequence level when aligned to framework sequences FR1, FR2, and FR3 of the original non-human heavy and light chain variable domains. Optionally, further parameters may be used to validate the selection for germline sequences with high identity. Examples for such parameters comprise the Smith-Waterman score and the E (expectation) value.

The antibodies or fragments thereof according to the invention are preferentially produced by recombinant means. Such methods are widely known in the state of the art and comprise protein expression in prokaryotic and eukaryotic cells, preferentially in non-mammalian cells, with subsequent isolation of the antibody polypeptide (full antibody or fragment thereof). The purification of the antibody polypeptide may be performed to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, *Bacillus* or *E. coli* cells, and the antibody is recovered from the cells (from the supernatant or after full or partial cells lysis). Recombinant production of antibodies is well-known in the state of the art.

The term "therapeutic effective amount" means an amount which provides a therapeutic benefit.

The term "isolated" means altered or removed from the natural state. For example an isolated population of cells means an enrichment of such cells and separation from other cells which are normally associated in their naturally occurring state with said isolated cells. An isolated population of cells means a population of substantially purified cells which are a homogenous population of cells.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

EMBODIMENTS

The antibody or fragment thereof of the invention may by be presented in various embodiments as disclosed herein and described in detail in the preceding sections. Common to all these embodiments of the humanized antibody or fragment thereof specific for the antigen CD45R0 is the existence of the CDR1 to CDR6 as given in SEQ ID NO:1 to SEQ ID NO:6, in the humanized heavy and light chain variable domains, respectively.

In one embodiment, an antibody or fragment thereof has CDR sequences (e.g., an IMGT®, Chothia, or Kabat CDR) that differ from those of the murine CD45R0 antibody clone UCHL1. CDR sequences that differ from those of murine CD45R0 antibody clone UCHL1 include amino acid changes, such as substitutions of 1, 2, 3, or 4 amino acids if a CDR is 5-7 amino acids in length, or substitutions of 1, 2, 3, 4, 5, 6, or 7 of amino acids in the sequence of a CDR if a CDR is 10 amino acids or greater in length. The amino acid that is substituted can have similar charge, hydrophobicity, or stereochemical characteristics. In some embodiments, the amino acid substitution(s) is a conservative substitution. In other embodiments, the amino acid substitution(s) is a non-conservative substitution. Such substitutions are within the ordinary skill of an artisan. The antibody or antibody fragments thereof that contain the substituted CDRs can be screened to identify antibodies binding to CD45R0 antigen.

In one embodiment of the invention a humanized antibody or fragment thereof as disclosed herein may be used for enrichment (positive selection) of CD45R0-expressing (CD45R0+) cells from a sample comprising CD45R0-expressing cells. In a preferred environment, the sample comprises CD45R0-expressing cells and CD45R0 non-expressing cells (other cells). Methods suited for enrichment are well known in the art and include but are not limited to flow cytometry such as FACS® or magnetic cell separation such as MACS®. The enriched CD45R0-expressing cells may be used in further various studies such as cytokine expression or receptor signaling or may be used in a pharmaceutical composition comprising these CD45R0-expressing cells. The enriched CD45R0-expressing cells may be expanded in vitro to a therapeutic effective amount prior to application to a patient in need thereof.

Exemplarily the principle of MACS® separation (Miltenyi Biotec GmbH, Germany) is described here: Antibodies or fragments thereof specific for CD45R0 antigen can be used for direct or indirect magnetic labeling of lymphocyte subsets. CD45R0 antigen is brightly expressed on CD4+ and CD8+ T cell subsets, and in a lower amount on monocytes, macrophages and granulocytes. First the CD45R0-expressing cells are magnetically labeled with CD45R0 MicroBeads, i.e. CD45R0 antibodies or fragments thereof conjugated to magnetic particles. Then the cell suspension is loaded on a MACS® Column which is placed in the magnetic field of a MACS® Separator. The magnetically labeled CD45R0-expressing cells are retained on the column. The unlabeled cells run through, this cell fraction is depleted of CD45R0+ cells. After removal of the column from the magnetic field, the magnetically retained CD45R0+ cells can be eluted as the positively selected cell fraction.

For isolation of CD45R0+ T cell subsets the antibodies or fragments thereof specific for CD45R0 can be combined for example with antibodies specific for CD4, CD8, CD19, CD25, and CD62L antigen, respectively.

In one embodiment of the invention a humanized antibody or fragment thereof as disclosed herein may be used for depletion of CD45R0-expressing cells from a sample comprising CD45R0-expressing cells. In a preferred environment, the sample comprises CD45R0-expressing cells and CD45R0 non-expressing cells (other cells). Methods suited for depletion are well known in the art and include but are not limited to flow cytometry such as FACS® or magnetic cell separation such as MACS®.

Some examples of applications in the context of enrichment (positive selection) and depletion of cells using the antibodies or fragments thereof as disclosed herein might be: (a) Depletion of human CD45R0+ cells from peripheral blood or lymphoid tissue for further selection of CD45R0 naïve T cell subsets. (b) Positive selection or depletion of human CD45R0+ memory T cells from preselected CD4+ or CD8+ cells isolated from peripheral blood or from lymphoid tissue. (c) Isolation of human CD45RA+ naïve T cells from presorted CD4+ or CD8+ cells by depletion of CD45R0+ cells.

The invention comprises a method for the treatment of a patient in need of therapy, characterized by administering to the patient a therapeutically effective amount of cells which were in contact with the antibody or fragment thereof according to the invention.

The invention comprises the use of an antibody according to the invention for cellular therapy, for example the isolation of CD45R0-positive memory T cells, optionally the expansion and afterwards the transfer of these cells to a patient. Another example is the depletion of CD45R0-positive memory T cells for the treatment of HIV because in humans it has been reported that a major site of the latent reservoir of HIV is within CD4-positive T cells expressing CD45R0, defined by the antibody UCHL1 (Valentine et al. (2013) PLoS ONE 8: e73969).

In one embodiment of the invention a humanized antibody or fragment thereof as disclosed herein may be used in a kit for enrichment or depletion of CD45R0+ cells, the kit providing
a) the humanized antibody of fragment thereof specific for the CD45R0 antigen; and
b) at least a second antibody or fragment thereof specific for a second antigen, wherein said second antigen is selected from the group consisting of CD4, CD8, CD19, CD25, CD45RA, and CD62L antigen. Said humanized antibody or fragment thereof specific for the CD45R0 antigen and said second antibody or fragment thereof specific for a second antigen may be coupled to a tag. Said tag may be a magnetic particle or a fluorophore. In one embodiment, the kit provides more than one antibody different from the humanized CD45R0 antibody, for example additional antibodies against CD8, and/or CD19, and/or CD25 antigen. Preferentially, the antibodies or fragments thereof provided in said kit may be sterile and usable for clinical applications.

In one embodiment of the invention a humanized antibody or fragment thereof as disclosed herein may be used for the isolation of naïve regulatory T cells. Using peripheral blood or lymphoid tissue, CD45R0-positive cells are depleted. Optionally, CD8-positive and/or CD19-positive cells are also depleted. In the next step, CD25-positive cells are enriched, resulting in isolated naïve regulatory T cells.

In one embodiment of the invention a humanized antibody or fragment thereof as disclosed herein may be used for the isolation of naïve T cells. Using peripheral blood or lymphoid tissue, CD45R0-positive cells are depleted. In the next step, CD62L-positive cells are enriched, resulting in isolated naïve T cells. These cells may be used for the generation of CAR (chimeric antigen receptor) T cells, for example by lentiviral or retroviral transduction of these cells.

In one embodiment of the invention a humanized antibody or fragment thereof as disclosed herein may be used for the fluorescent labeling of cells expressing CD45R0. This may be accomplished in vitro (e.g. in cell culture) or in vivo (e.g. in the body). The fluorescent label may be attached to the antibody or fragment thereof directly (e.g. by chemical conjugation) or indirectly (e.g. by biotinylation of the humanized antibody or fragment thereof and binding of the biotinylated antibody to a streptavidin fluorochrome conjugate).

In one embodiment of the invention a humanized antibody or fragment thereof as disclosed herein may be used for the identification and monitoring of memory T cells in vitro or in vivo. For example, it has been shown that murine CD45R0 antibody clone UCHL1 reacts with macaque memory T cells. Therefore, humanized forms of UCHL1 may provide an immunological tool for macaque in vivo models.

The cell compositions enriched and/or separated by the use of antibodies or fragments thereof as disclosed herein may be administered either alone, or as a pharmaceutical composition in combination with diluents and/or with other components such cytokines. Briefly, pharmaceutical compositions of the present invention may comprise a cell composition enriched and/or separated by use of an antibody or fragment thereof as disclosed herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Preferentially, the compositions of the present invention are formulated for intravenous administration. The administration of cell compositions to the subject may be carried out in any convenient manner known in the art.

Pharmaceutical compositions of the present invention may be administered in a manner appropriate to the disease to be treated. Appropriate dosages may be determined by clinical trials. But the quantity and frequency of administration will also be determined and influenced by such factors as the condition of the patient, and the type and severity of the patient's disease.

In one embodiment of the invention, humanized antibodies or fragments thereof against CD45R0 are less immunogenic when administered to human patients compared to non-humanized antibodies or fragments thereof, and therefore they may be useful for clinical and cell therapeutic purposes.

In one embodiment of the invention, humanized antibodies or fragments thereof against CD45R0 are more stable than non-humanized antibodies or fragments thereof. Recombinant expression levels may be higher for a more stable antibody variant, resulting in a higher antibody yield after purification. The increased stability may be also beneficial for use of a purified antibody or fragment thereof in clinical and cell therapeutic purposes due to an increased half-life and/or less degradation of the antibody.

EXAMPLES

Example 1

In Silico Aggregation Analysis of Parental Murine CD45R0 Antibody Clone UCHL1

Figures 1A, 1B:
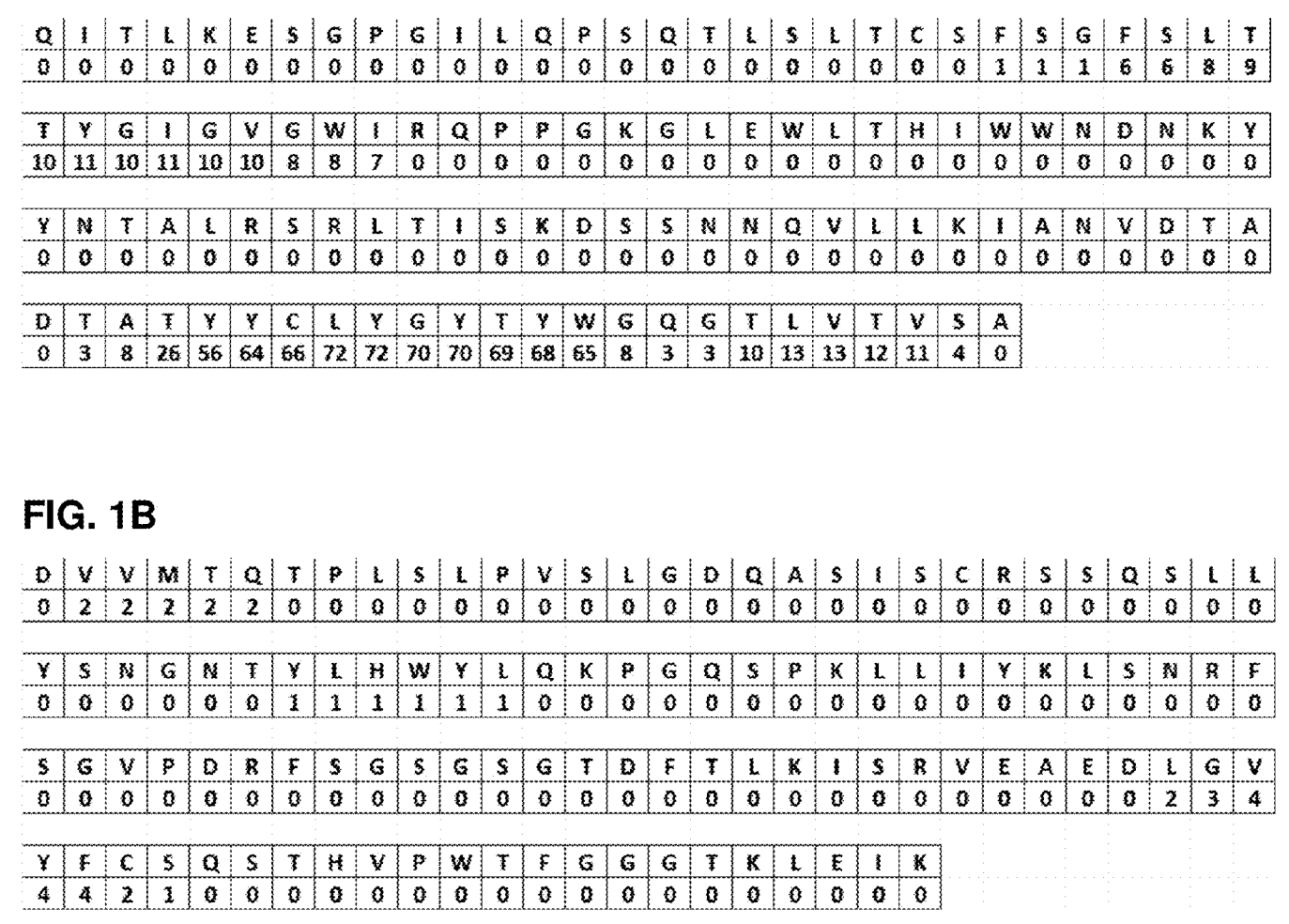

The amino acid sequences of heavy and light chain variable domains of CD45R0 antibody clone UCHL1 were analyzed using algorithms known-in-the-art to predict sequence regions which are prone to aggregation. It is known that such regions may interfere with the recombinant expression of a protein which results in low protein expression levels. Useful algorithms comprises for example PASTA (Walsh et al. (2014) Nucleic Acids Res. 42, W301-307), WALTZ (Maurer-Stroh et al. (2010) Nature Methods 7, 237-242), and AGGRESACN (Conchillo-Solé et al. (2007) BMC Bioinformatics 8, 65-81). The algorithms typically assign a numerical score to each amino acid, wherein the score is an indicator for the aggregation potential. FIG. 1 shows the assignment of such a score to the heavy chain (of SEQ ID NO:13, FIG. 1A) and light chain (of SEQ ID NO:14, FIG. 1B) variable domains of murine CD45R0 antibody clone UCHL1. A score of 0 indicates no, a score of about >20 indicates a moderate and a score of about >50 indicates a high tendency to form aggregates. In the case of CD45R0 antibody clone UCHL1, a tyrosine-rich region with the sequence TYYCLYGYTYW (SEQ ID NO:30) comprising CDR3 (SEQ ID NO:3) of heavy chain variable domain is predicted to be highly aggregation-prone. It was therefore expected that the recombinant expression of CD45R0 antibody clone UCHL1 and also of humanized variants thereof comprising CDR3 (SEQ ID NO:3) would result in only low expression levels and product titers.

Example 2

Humanization of CD45R0 Antibody Clone UCHL1 by CDR Grafting into Human Germline Framework Sequences The CDRs and the numbering of the amino acid residues according to the IMGT® nomenclature were determined by submitting the heavy and light chain sequences of the parental murine CD45R0 antibody clone UCHL1 to the IMGT® "DomainGapAlign" tool (see world wide web at.imgt.org/3Dstructure-DB/cgi/DomainGapAlign.cgi). The resulting numbering schemes and CDR definitions are depicted in FIG. 9A and FIG. 9B and in SEQ ID NO:1 to SEQ ID NO:6. In a next step, the amino acid sequences of the light and heavy chains of the parental murine CD45R0 antibody clone UCHL1 were compared against reference databases of human germline V regions (polypeptide sequences). The current versions (January 2014) of the IMGT® human IG reference directory sets were used as reference databases (see http://www.imgt.org/vquest/refseqh.html for an overview), for IGHV: see world wide web at.imgt.org/IMGT_GENE-DB/GENElect?query=7.6+IGHV&species=Homo+sapiens; for IGKV: see world wide web at imgt.org/IMGT_GENE-DB/GENElect?query=7.6+IGKV&species=Homo+sapiens. These sequences include FR1, CDR1, FR2, CDR, and FR3, but not CDR3 and FR4. CDR3 of the heavy chain is primarily assembled from a small part of a V segment, the whole D segment and a small part of a J segment. CDR3 of the light chain is primarily assembled from a small part of a V segment and a small part of a J segment. FR4 is derived from the J segment. Prior to further processing, pseudogenes and duplicate sequences were removed from the IMGT® reference sets. For the identification of human germline sequences with high identity to the framework regions of the original non-human heavy and light chain variable domains, the identity of framework regions FR1, FR2, and FR3, and of CDR1 and CDR2 were compared at the amino acid level against the processed IMGT® reference sets by using the Smith-Waterman algorithm implemented in the ssearch36 program which is part of the FASTA36 package (see world wide web at faculty.virginia.edu/wrpearson/fasta/). For the heavy chain, the allele IGHV2-5*01 of the V segment (SEQ ID NO:23) returned the highest percentage identity. It also returned the highest Smith-Waterman score and the lowest E-value, and was selected as template for CDR grafting. For the light chain variable domain, the allele IGKV2-30*01 of the V segment (SEQ ID NO:24) returned the highest percentage identity. It also returned the highest Smith-Waterman score and the lowest E-value, and was selected as template for CDR grafting. In principle, FR4 may also be included into sequence comparison for humanization using the IMGT® reference set of IGHJ or IGKJ segments. FR4 of the parental clone UCHL1 heavy chain differs from the amino acid sequence encoded by the human J segment with highest identity (IGHJ5*02, SEQ ID NO:25) only by a single conservative amino acid exchange, and therefore this framework region was not subjected to humanization. The same applies to the UCHL1 light chain (human J segment with highest identity: IGKJ4*01, SEQ ID NO:26). Finally, the CDRs (according to the IMGT® definition) of the selected human germline template sequences IGHV2-5*01 and IGKV2-30*01 were replaced by the CDRs of the parental murine CD45R0 antibody clone UCHL1 (SEQ ID NO:1-6), resulting in SEQ ID NO:17 and SEQ ID NO:18.

In order to identify amino acid residues in the framework regions FR1, FR2, and FR3 of the CDR-grafted human germline sequences (SEQ ID NO:17 and SEQ ID NO:18) which differ from the parental murine CD45R0 antibody clone UCHL1 (SEQ ID NO:13 and SEQ ID NO:14), pairwise alignments between these sequences were generated using the LALIGN program (for example see world wide web at .ch.embnet.org/software/LALIGN_form.html). FIG. 2 shows the sequence alignment of FR1, CDR1, FR2, CDR2, and FR3 of the heavy chain variable domain of the parental murine CD45R0 antibody clone UCHL1 ("HC_muCD45R0", which is identical to SEQ ID NO:13 without CDR3 and FR4) and the amino acid sequence encoded by the allele IGHV2-5*01 of the human germline V segment after substitution of its CDR regions by the CDR regions of the parental murine CD45R0 antibody clone UCHL1 ("gr_IGHV2-5*01"; SEQ ID NO:27, which is SEQ ID NO:23 without CDR3 and with CDR1 and CDR2 substituted by SEQ ID NO:1 and SEQ ID NO:2, respectively). FIG. 3 shows the sequence alignment of FR1, CDR1, FR2, CDR2, and FR3 of the light chain variable domain of the parental murine CD45R0 antibody clone UCHL1 ("LC_muCD45R0", which is identical to SEQ ID NO:14 without CDR3 and FR4) and the amino acid sequence encoded by the allele IGKV2-30*01 of the human germline V segment after substitution of its CDR regions by the CDR regions of the parental murine CD45R0 antibody clone UCHL1 ("gr_IGKV2-30*01", SEQ ID NO:28, which is identical to SEQ ID NO:24 without CDR3 and with CDR1 and CDR2 substituted by SEQ ID NO:4 and SEQ ID NO:5, respectively). Amino acid residues within the framework regions which physically interact (by hydrogen bonds, electrostatic, hydrophobic, or other interactions) with amino acid residues within the CDR regions ("Vernier residues") and which are different between the parental murine CD45R0 antibody clone UCHL1 and the human template germline sequence may be critical for antigen binding and structural integrity of the humanized antibody. Those residues have to be backmutated, i.e. the respective amino acid residue within the CDR-grafted sequence has to be replaced by the corresponding amino acid at the same position within the parental murine CD45R0 antibody clone UCHL1. The identification of amino acid residues suitable for backmutation requires knowledge about the three-dimensional structure of the antibody to be modified. As no structural data for the parental murine CD45R0 antibody clone UCHL1 was available, an alternative antibody with a high sequence identity to the parental murine CD45R0 antibody clone UCHL1 was used. For that purpose, BLAST searches of the light and heavy chain sequences of UCHL1 against the PDB protein database (see the world wide web at pdp.com) were conducted, and structures with corresponding peptide sequences that show the highest bit score and the lowest E-values were selected separately for light and heavy chain. For the heavy chain, the structure 3U9U (chain A, http://www.pdb.org/pdb/explore/explore.do?structureId=3U9U) and for the light chain, the structure 1T66 (chain C, see the world wide web at pdb.org/pdb/explore/explore.do?structureId=1T66) was selected, respectively. For the structure-based analysis the publicly available software "Discovery Studio 4.0" (Accelrys) was used. Firstly, the CDRs according to the IMGT® nomenclature were defined within the structure and all framework atoms within a radius of 5 Å of the CDRs were labeled. Subsequently, each framework amino acid identified by this procedure was checked for its conservation between the human template and the parental murine CD45R0 antibody clone UCHL1. Using this procedure, amino acids specifically interacting with the CDRs and probably stabilizing their structure were identified and backmutated in the corresponding human CDR grafted germline sequence. FIG. 4 shows the sequence alignment of FR1, CDR1, FR2, CDR2, and FR3 of the heavy chain variable domain encoded by the allele IGHV2-5*01 of the human germline V segment after substitution of its CDR regions by the CDR regions of the parental murine CD45R0 antibody clone UCHL1 ("gr_IGHV2-5*01", SEQ ID NO:27) and the final humanized sequence of the heavy chain variable domain of the CD45R0 antibody including backmutations, CDR3 and FR4 ("HC_final", SEQ ID NO:7). FIG. 5 shows the sequence alignment of FR1, CDR1, FR2, CDR2, and FR3 of the light chain variable domain encoded by the allele IGKV2-30*01 of the human germline V segment after substitution of its CDR regions by the CDR regions of the parental murine CD45R0 antibody clone UCHL1

("gr_IGKV2-30*01", SEQ ID NO:28) and the final humanized sequence of the light chain variable domain of the CD45R0 antibody including backmutations, CDR3 and FR4 ("LC_final", SEQ ID NO:8).

For the expression of non-humanized and humanized Fab fragments against CD45R0 in *E. coli*, synthetic genes encoding for non-humanized and humanized heavy chain and light chain variable domains (designated as VH and VL) of CD45R0 clone UCHL1 (SEQ ID NO:7 in combination with SEQ ID NO:8; SEQ ID NO:9 in combination with SEQ ID NO:10; SEQ ID NO:11 in combination with SEQ ID NO:12; SEQ ID NO:13 in combination with SEQ ID NO:14), for human kappa light chain constant region (designated as CL, SEQ ID NO:22), and for human IgG1 heavy chain constant region CH1 (SEQ ID NO:21) were designed using a standard software tool. Compatible flanking restriction sites were added to the synthetic genes sequences to facilitate direct cloning into an *E. coli* expression vector. Gene synthesis was performed externally by a service provider. The gene sequence encoding for the light chain (LC) variable domain (VL and CL) of the Fab fragment comprises a phoA signal sequence for periplasmatic translocation of the light chain. The gene sequence encoding for the heavy chain (HC) variable domain (VH and CH1, optionally followed by a poly-histidine tag) of the Fab fragment comprises a pelB signal sequence for periplasmatic translocation of the heavy chain. Cloning was performed using standard techniques known in the art. The resulting *E. coli* expression vector is shown in FIG. 6. All vector regions affected by the cloning procedure were validated by DNA sequencing.

Example 5

Expression of Fab Fragments Against CD45R0 Antigen in *E. coli*

For production of Fabs against CD45R0, *E. coli* W3110 cells were transformed with an appropriate expression vector such as, for example, "pOPE313 huCD45R0_v3" which encodes for the humanized variant "huCD45R0_v3" with heavy chain (VH) and light variable (VL) domains as described in SEQ ID NO:7 and SEQ ID NO:8. Pre-cultures of transformed *E. coli* were grown in complex media (containing soy-peptone, yeast extract and NaCl, supplemented with glucose) in shake flasks over night at 37° C. The next morning, a stirrable lab-scale bioreactor (3 L) containing complex media (containing soy-peptone, yeast extract and NaCl, supplemented with glucose as carbon source) was inoculated to a final optical density at 600 nm of 0.05 using the pre-culture. The cells were grown at 28° C. and pH 7.0 with a $pO_2$ of at least 30%. Before induction the bioreactor was cooled to 25° C. and target protein expression was subsequently induced by addition of 0.2 mM IPTG. The cultivation was continued for at least 20 h at 25° C. Glucose was constantly added as carbon source, and pH was kept at 7.0. Cell harvest was performed by centrifugation at 6000×g for 1 hour. Harvested cell pellets were stored at −20° C. for further processing.

Example 6

Purification of Fab Fragments Against CD45R0 Antigen

Figure 7:
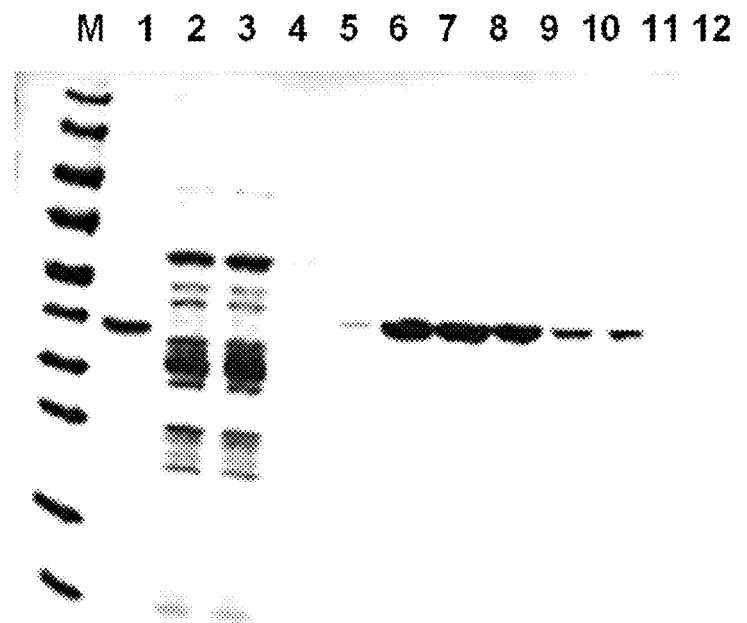
FIG. 7 shows a Coomassie-stained SDS gel with samples of different steps of the purification of Fab variant "huCD45R0_v3" by metal chelate affinity chromatography. M, molecular weight marker with sizes of 170, 130, 100, 70, 55, 40, 35, 25, 15, and 10 kDa. Lane 1: 2 µg Fab reference; lane 2: periplasmic extract; lane 3: flow-through fraction; lane 4: wash fraction; lanes 5-12: eluate fractions.

Recombinant Fabs against CD45R0 were purified from fermented *E. coli* cells of example 5 by a periplasmic extraction step followed by chromatographic purification steps. For cell extraction, frozen *E. coli* pellets were resuspended in 10 mL of periplasmic extraction buffer (100 mM Tris, 10 mM EDTA) per 1 g cell pellet (wet weight) and incubated at 37° C. with constant agitation for at least 16 h. Afterwards the suspension was centrifuged at 6000×g for 1 hour. The supernatant contained the periplasmic fraction of *E. coli*, harboring the Fabs. Cell pellets were discarded. The supernatant was filtered and applied to a suitable chromatography column packed with an IMAC resin (for example ProCatchHis Resin, Miltenyi Biotec) for metal chelate affinity chromatography on an FPLC system (ÄKTA) for a first affinity capture purification step. Impurities were washed away using imidazole-containing buffer (5 mM). The target protein was eluted using a buffer containing an increased imidazole concentration of at least 50 mM. Eluted fractions were pooled and applied to a cation exchange matrix (for example SP sepharose). Elution was performed using a phosphate (25 mM) based buffer in the pH range of 6.0-7.4 containing NaCl in the range of 0.3-0.5 M. Eluates containing Fabs were pooled and the protein content was quantified by BCA assay and UV absorption ($A_{280}$ nm). Aliquots of purified Fabs against CD45R0 were stored at −80° C. towards use. FIG. 7 shows a Coomassie-stained SDS gel with samples of different steps of the purification process of Fab variant "huCD45R0_v3" as an example. Table 1 lists the amount of purified Fabs from 100 g *E. coli* cell pellet. Because the expression and purification process was nearly identical for all variants, the amount of purified Fabs is a good indicator for the individual expression level of a Fab variant. The highest amount of protein after purification was found for the humanized Fab variant "huCD45R0_v3", which shows that the expression level variant "huCD45R0_v3" was also the highest of all tested variants.

TABLE 1

Yield of purified Fab variants against CD45R0 (from 100 g *E. coli* cell pellet). The yield of the Fab variant "muCD45R0" was set to 100%.

| Variant | mg purified protein | yield (%) |
| --- | --- | --- |
| muCD45R0 | 2.5 | 100 |
| huCD45R0_v1 | 0.8 | 32 |
| huCD45R0_v2 | 1.4 | 56 |
| huCD45R0_v3 | 7 | 280 |

Example 7

Magnetic Isolation of CD45R0-Expressing Cells from PBMC Using Fab Variants "muCD45R0" and "huCD45R0_v3"

Figure 8:
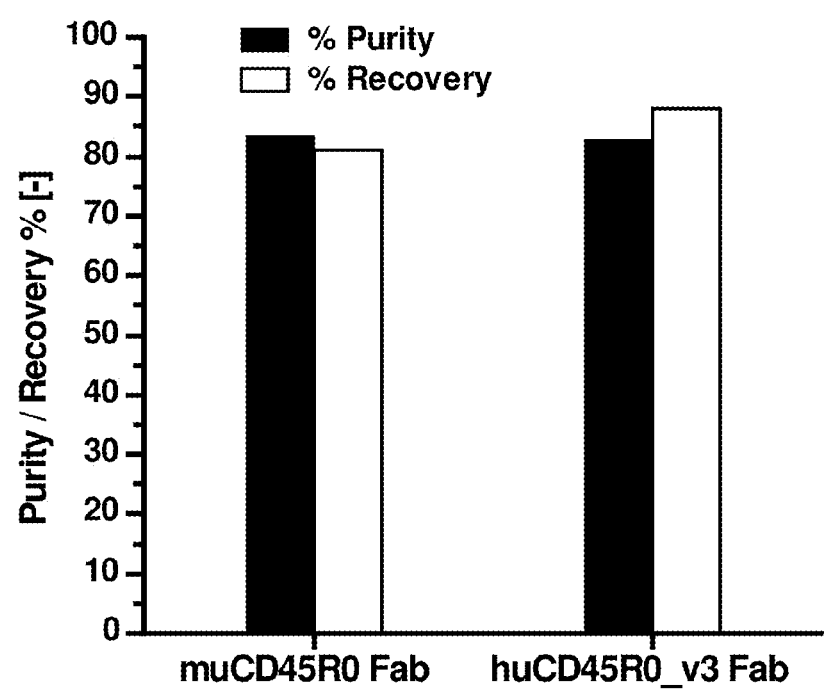
FIG. 8 shows magnetic isolation of CD45R0-expressing cells from PBMC using Fab variants "muCD45R0" and "huCD45R0_v3". Purified biotinylated Fabs against CD45R0 were used in combination with magnetic anti-Biotin-MicroBeads to isolate CD45R0-expressing cells from human PBMC. "% purity" represents the number of CD45R0-positive cells within the "pos" fraction compared to the number of all living lymphocytes in the "pos" fraction. "% recovery" represents the number of CD45R0-positive cells within the "pos" fraction compared to the number of CD45R0-positive cells in the "ori" fraction.

Purified biotinylated Fabs against CD45R0 were used in combination with magnetic anti-Biotin-MicroBeads (Miltenyi Biotec) to isolate CD45R0-expressing cells from human PBMC. Therefore, purified Fabs of example 6 were chemically biotinylated using standard techniques known in the art. Cells were incubated with purified biotinylated Fab variants "muCD45R0" and "huCD45R0_v3", respectively, at 5 μg/mL for 10 min at 4° C. To wash the cells, phosphate buffer/EDTA/0.5% BSA was added, the cells were centrifuged at 300×g at 4° C., the supernatant was discarded and the cells were resuspended in phosphate buffer/EDTA/0.5% BSA. Then anti-Biotin-MicroBeads were added and the mixture was incubated for 10 min at 4° C. For a subsequent flow cytometric analysis to measure the separation success, CD45RA antibody-APC-conjugate, CD3 antibody-FITC-conjugate, CD45R0 antibody-PE (phycoerythrin)-conjugate, and anti-Dextran-antibody-FITC-conjugate were additionally added in volumes and concentrations recommended by the manufacturer (Miltenyi Biotec) and incubated for 5 min at 4° C. To wash the cells, phosphate buffer/EDTA/0.5% BSA was added, the cells were centrifuged at 300×g at 4° C., the supernatant was discarded and the cells were resuspended phosphate buffer/EDTA/0.5% BSA. The cells were then magnetically separated using MACS® technology with an LS-column (Miltenyi Biotec) according to the manufacturer's instructions. The original ("ori"), the positive ("pos") and the negative ("neg") fractions of the magnetic separation process were analyzed using flow cytometry. Gating was applied on living lymphocytes, and cells were analyzed regarding the expression of CD3, CD45RA, and CD45R0 and regarding the labeling of cells with magnetic beads by staining the dextran envelope of the beads. FIG. 8 shows purity and recovery of CD45R0-positive cells after magnetic separation. "% purity" represents the number of CD45R0-positive cells within the "pos" fraction compared to the number of all living lymphocytes in the "pos" fraction. "% recovery" represents the number of CD45R0-positive cells within the "pos" fraction compared to the number of CD45R0-positive cells in the "ori" fraction.

Figure 9:
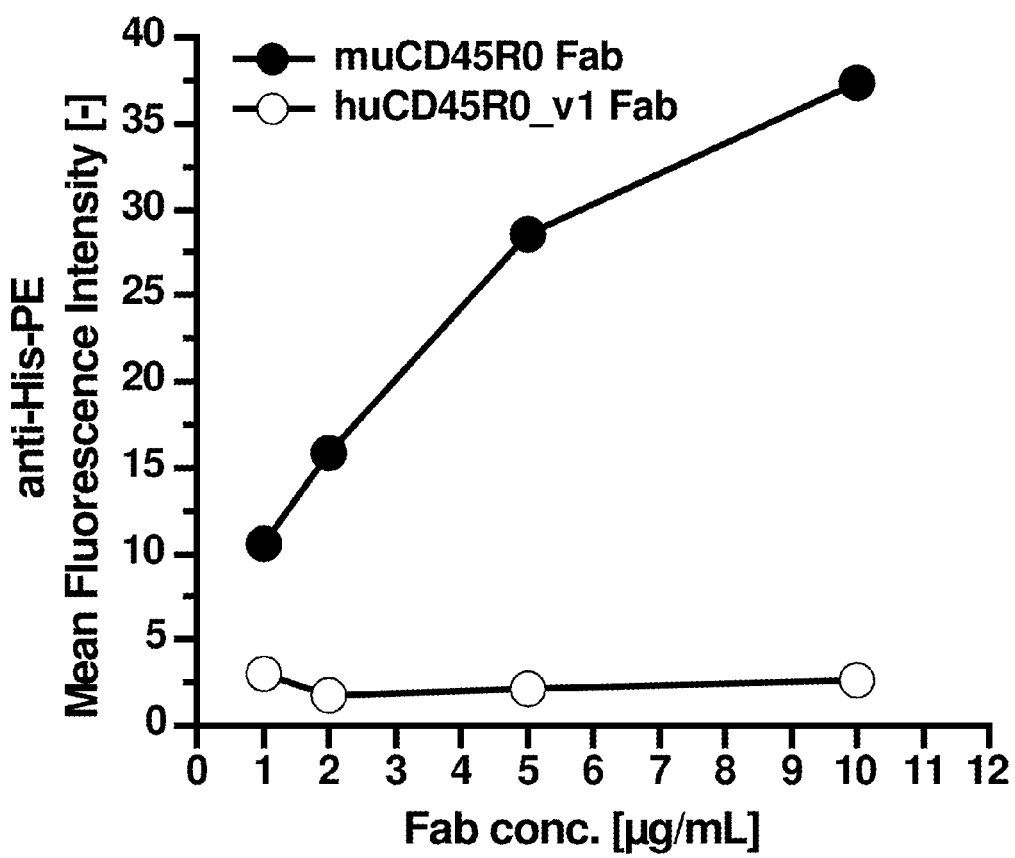
FIG. 9 shows flow cytometric analysis of human PBMC stained with Fab variants "muCD45R0" and "huCD45R0_v1". Purified Fabs against CD45R0 were used in combination with an anti-His-PE conjugate for an indirect staining of human PBMC. The mean fluorescence intensity (MFI) of anti-His-PE is plotted against the Fab concentration.

Purified Fabs against CD45R0 of example 6 were used in combination with an anti-His-PE (anti-polyhistidine-PE) conjugate (Miltenyi Biotec) for the indirect staining of CD45R0-expressing cells in human PBMC. The cells were incubated with 1-10 µg/mL of Fab variants "muCD45R0" and "huCD45R0_v1", respectively, for 10 min at 4° C. To wash the cells, phosphate buffer/EDTA/0.5% BSA was added, the cells were centrifuged at 300×g at 4° C., the supernatant was discarded and the cells were resuspended phosphate buffer/EDTA/0.5% BSA. Cell-bound Fabs against CD45R0 were detected with an anti-His-PE conjugate in an appropriate dilution (according to the manufacturer's instructions). Gating was applied on living white blood cells (WBCs). The mean fluorescence intensity (MFI) of anti-His-PE is plotted against the Fab concentration. FIG. 9 shows the MFI values for Fab variants "muCD45R0" and "huCD45R0_v1" in concentrations of 1-10 µg/mL. In table 2, the relative affinity of "huCD45R0_v1" compared to "muCD45R0" based on the maximum MFI values is calculated.

TABLE 2

Relative affinity of Fab variants "huCD45R0_v1" and "muCD45R0" towards cell-bound CD45R0. The relative affinity of the Fab variant "muCD45R0" was set to 100%.

| Variant | max. mean fluorescence (anti-HIS-PE) | relative affinity (%) |
|---|---|---|
| muCD45R0 | 37 | 100 |
| huCD45R0_v1 | 3 | 8 |

Example 9

Flow Cytometric Analysis of Human PBMC Stained with Fab Variants "muCD45R0", "huCD45R0_v2", and "huCD45R0_v3"

Figure 10A:
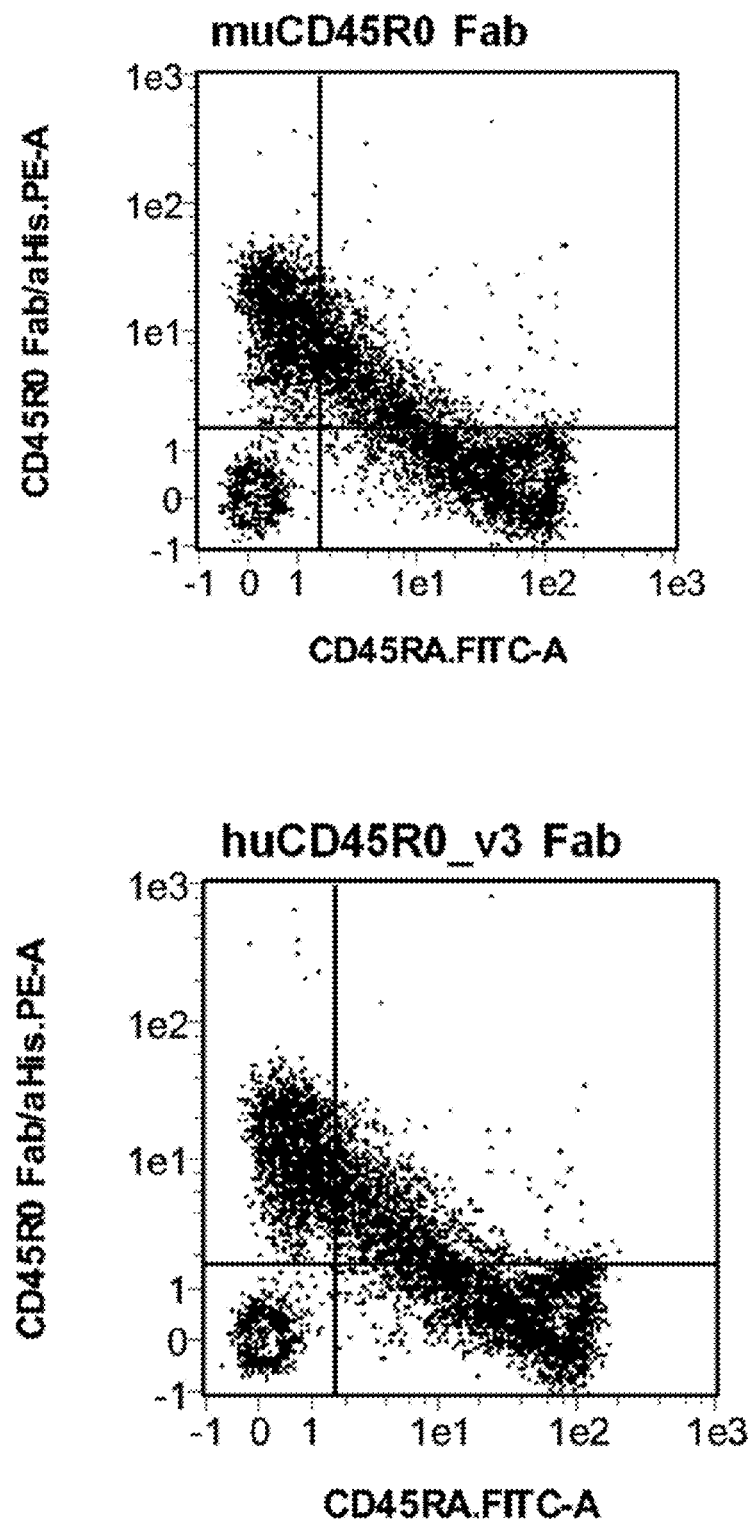
FIG. 10A and FIG. 10B show flow cytometric analysis of human PBMC stained with Fabs against CD45R0. Purified Fabs were used in combination with an anti-His-PE conjugate for an indirect staining of human PBMC.
Figure 10B:
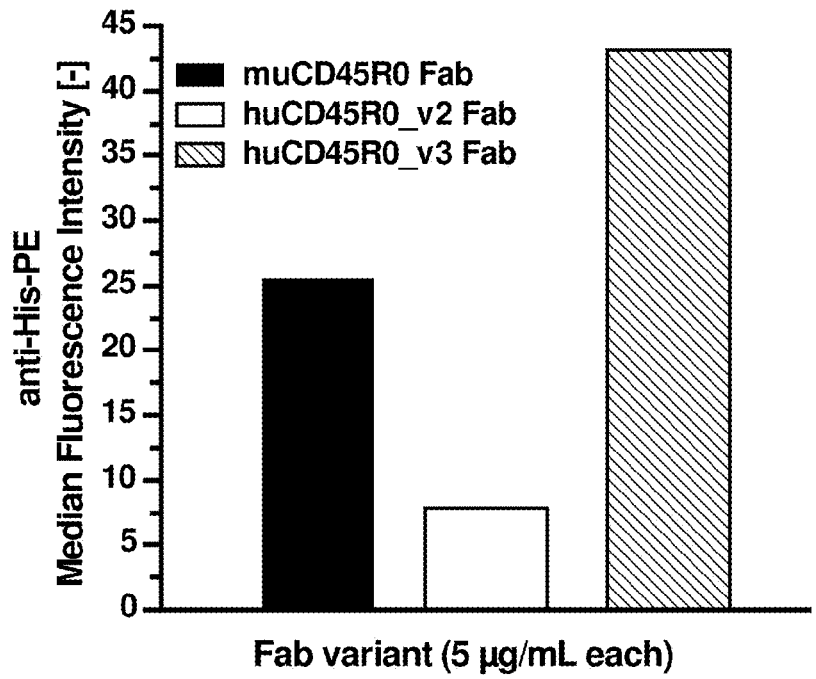

Purified Fabs against CD45R0 of example 6 were used in combination with an anti-His-PE conjugate for the indirect staining of CD45R0-expressing cells in human PBMC. The cells were incubated for 10 min at 4° C. with either Fab variant "muCD45R0", "huCD45R0_v2", or "huCD45R0_v3" at a concentration of 2 to 5 µg/mL, and additionally with anti-CD45RA-FITC conjugate (dilution according to manufacturer's instructions). To wash the cells, phosphate buffer/EDTA/0.5% BSA was added, the cells were centrifuged at 300×g at 4° C., the supernatant was discarded and the cells were resuspended phosphate buffer/EDTA/0.5% BSA. Cell-bound Fabs against CD45R0 were detected with an anti-His-PE conjugate in an appropriate dilution (according to manufacturer instructions). Gating was applied on living CD45RA-negative white blood cells (WBCs). FIG. 10A shows a dot plot of Fab variants "muCD45R0" and "huCD45R0_v3" (Fab+anti-His-PE) fluorescence vs. CD45RA-FITC fluorescence. No significant difference was detected between "muCD45R0" and "huCD45R0_v3". FIG. 10B shows the median fluorescence intensities for Fab variants "muCD45R0", "huCD45R0_v2", and "huCD45R0_v3" at a concentration of 5 µg/mL. In table 3, the relative affinity of "huCD45R0_v2" and "huCD45R0_v3" compared to "muCD45R0" based on the median fluorescence intensities is calculated.

TABLE 3

Relative affinity of Fab variants "huCD45R0_v2", "huCD45R0_v3", and "muCD45R0" towards cell-bound CD45R0. The relative affinity of the Fab variant "muCD45R0" was set to 100%.

| Variant | median fluorescence (anti-HIS PE) | relative affinity (%) |
|---|---|---|
| muCD45R0 | 26 | 100 |
| huCD45R0_v2 | 8 | 31 |
| huCD45R0_v3 | 43 | 165 |

Example 10

Flow Cytometric Analysis of Human T Cells within PBMC Stained with Fab Variants "muCD45R0" and "huCD45R0_v3"

Figure 11:
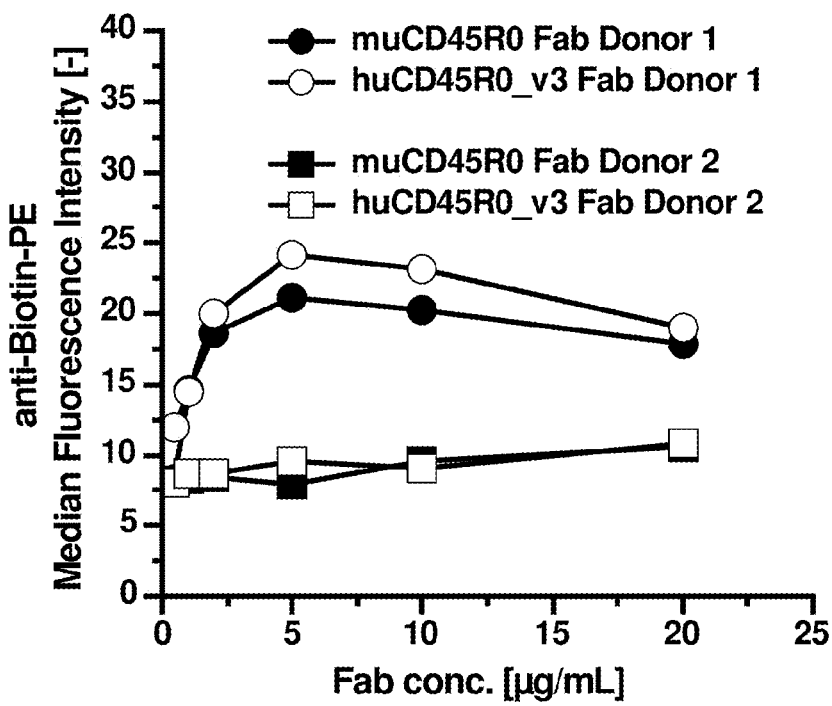
FIG. 11 shows flow cytometric analysis of human T cells stained with Fab variants "muCD45R0" and "huCD45R0_v3". Purified biotinylated Fabs against CD45R0 were used in combination with an anti-Biotin-PE conjugate for an indirect staining of human T-cells from two different donors (donor 1 and donor 2). The median fluorescence of anti-Biotin-PE is plotted against the Fab concentration.

Purified biotinylated Fabs against CD45R0 were used in combination with an anti-Biotin-PE-conjugate (Miltenyi Biotec) for indirect staining of CD45R0-expressing human T cells from two different donors. Therefore, purified Fabs of example 6 were chemically biotinylated using standard techniques known in the art. Human PBMCs were incubated with biotinylated Fab variants "muCD45R0" and "huCD45R0_v3", respectively, at concentrations of 0.5-20 µg/mL for 10 min at 4° C. For a subsequent flow cytometric analysis, additionally CD45RA antibody-APC-conjugate and CD3 antibody-FITC-conjugate (according to the manufacturer's instructions) were added. To wash the cells, phosphate buffer/EDTA/0.5% BSA was added, the cells were centrifuged at 300×g at 4° C., the supernatant was discarded and the cells were resuspended phosphate buffer/EDTA/0.5% BSA. Cell-bound Fabs against CD45R0 were detected using an anti-Biotin-PE-conjugate (Miltenyi Biotec) in an appropriate dilution (according to the manufacturer's instructions). Gating was applied on living CD3-positive, CD45RA-negative T-cells. The median fluorescence of anti-Biotin-PE is plotted against the Fab concentrations. FIG. 11 shows the median fluorescence intensities for Fab variants "muCD45R0" and "huCD45R0_v3" with concentrations of 0.5-20 µg/mL using cells of two different donors. In table 4, the relative affinity of "huCD45R0_v3" compared to "muCD45R0" based on the median fluorescence intensities at 5 µg/mL is calculated.

TABLE 4

Relative affinity of Fab variants "huCD45R0_v3" and "muCD45R0" towards cell-bound CD45R0. The relative affinity of the Fab variant "muCD45R0" was set to 100%.

| Variant | median fluorescence (anti-HIS-PE), donor 1 | median fluorescence (anti-HIS-PE), donor 2 | relative affinity (%) |
|---|---|---|---|
| muCD45R0 | 8 | 21 | 100 |
| huCD45R0_v3 | 9.5 | 24 | 114-119 |

Example 11

Flow Cytometric Analysis of Human PBMC Stained with Fab Variant "huCD45R0_v3", the Parental Antibody UCHL1 Against CD45R0 and an Antibody Against CD45RB To analyze whether the specificity of "huCD45R0_v3" is still restricted towards CD45R0 and not CD45RB (like the parental murine CD45R0 antibody clone UCHL1), blocking experiments utilizing suitable antibodies or antibody-conjugates were performed. For each staining experiment 1×10$^6$ human PBMCs were used. Cells were incubated with "huCD45R0_v3" of example 6 (2 µg/mL), CD45R0 antibody-PE conjugate (Miltenyi Biotec, clone UCHL1, titer 1:11), or CD45RB antibody-PE conjugate (Miltenyi Biotec, clone REA119, titer 1:11), respectively, for ten minutes at 4° C. An anti-His-PE conjugate (Miltenyi Biotec, titer 1:11) was added to the sample containing "huCD45R0_v3" which then was incubated for ten minutes at 4° C. to detect cell bound "huCD45R0_v3". Cells without Fab or antibody and cells with the anti-His-PE conjugate served as controls. To wash the cells, phosphate buffer/EDTA/0.5% BSA was added, the cells were centrifuged at 300×g at 4° C., the supernatant was discarded and the cells were resuspended in 1 mL phosphate buffer/EDTA/0.5% BSA. The samples were analyzed by flow cytometry. Gating was applied to analyze living cells only. The percentage of PE-positive cells was used for further analysis.

Figure 12:
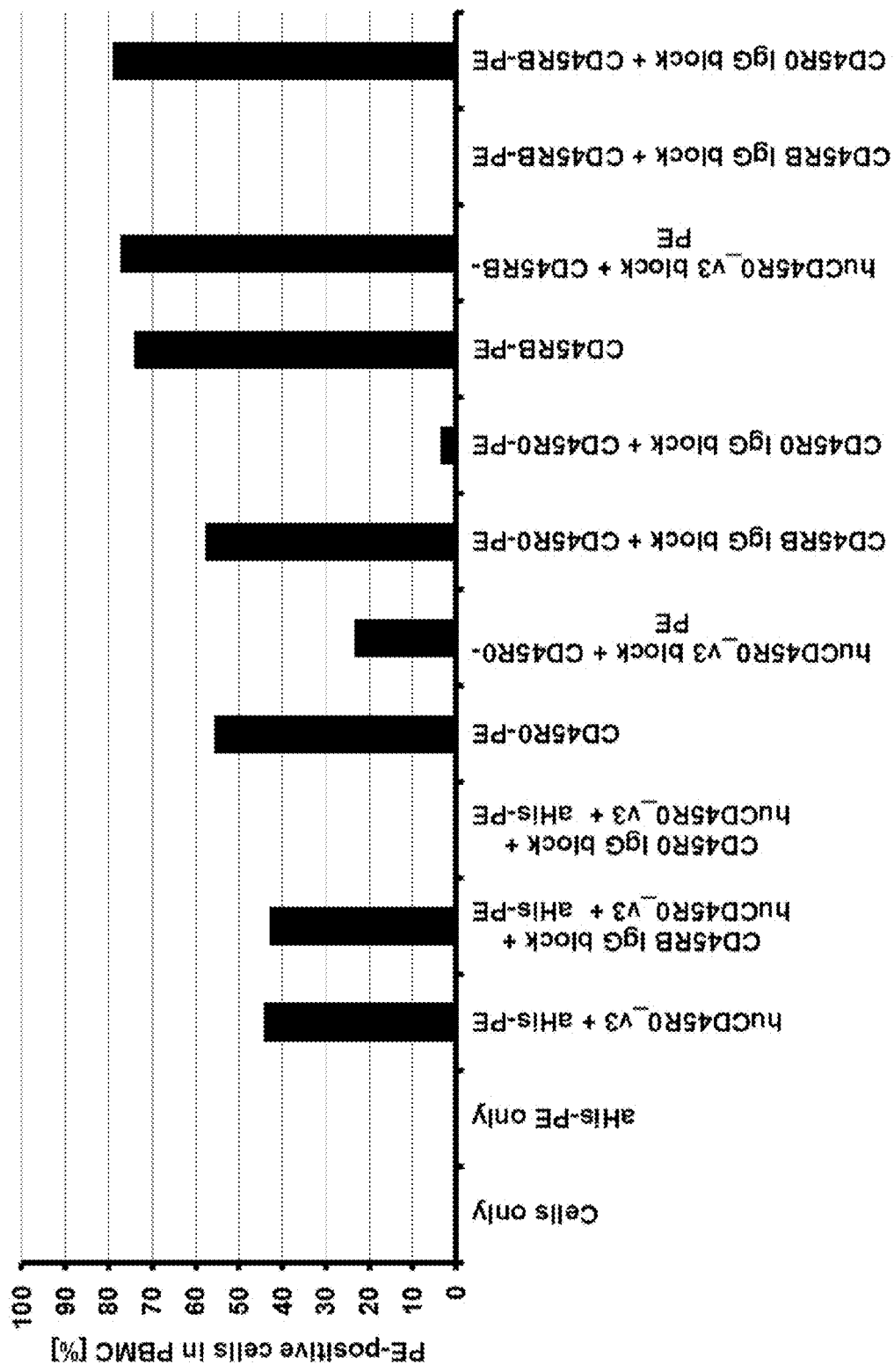
FIG. 12 shows flow cytometric analysis of human PBMC stained with Fab variant "huCD45R0_v3", the parental antibody UCHL1 against CD45R0 and an antibody against CD45RB. The percentage of PE-positive cells in PBMC is given. "Block" means that unconjugated antibody or Fab was added in excess to cells prior to the addition of antibody-PE conjugate or Fab+anti-HIS-PE (aHIS-PE) conjugate. "IgG" designates full-length antibody.

To analyze blocking of antibody or Fab binding, 100 µg of purified unconjugated IgG antibodies (clone UCHL1 against CD45R0 and Clone REA119 against CD45RB) or purified "huCD45R0_v3 Fab" were added to the cells (designated as "block") before adding either Fab/anti-His-PE conjugate or antibody-PE conjugate. The samples were incubated for ten minutes at 4° C. before staining. Afterwards the staining procedure was performed as described before. FIG. 12 shows that no blocking of CD45R0 antibody-PE conjugate or "huCD45R0_v3"+anti-His-PE conjugate was detected when an excess of CD45RB antibody was added in advance. However, a complete blocking of "huCD45R0_v3"+anti-His-PE conjugate could be achieved by adding an excess of CD45R0 antibody in advance. A partial blocking of CD45R0 antibody-PE conjugate resulted by adding an excess of "huCD45R0_v3" in advance, whereas the blocking of CD45R0 antibody-PE conjugate by adding an excess of CD45R0 antibody was almost complete. The incomplete blocking mediated by "huCD45R0_v3" Fab is explained by the lack of an avidity effect for "huCD45R0_v3" since this is a monovalent Fab-based reagent. No blocking of CD45RB antibody-PE conjugate was observed when an excess of either CD45R0 antibody or "huCD45R0_v3" were added in advance to the cells. As expected a complete blocking of CD45RB antibody-PE conjugate was achieved by adding an excess of CD45RB antibody. These results indicate that "huCD45R0_v3" is still specific towards the CD45R0 antigen but does not bind specifically to the CD45RB antigen.

```
                    Sequence listing

CDR1 of heavy chain variable domain
                                          SEQ ID NO: 1
GFSLTTYGIG CDR2 of heavy chain variable domain
                                          SEQ ID NO: 2
IWWNDNK CDR3 of heavy chain variable domain
                                          SEQ ID NO: 3
LYGYTY CDR1 of light chain variable domain
                                          SEQ ID NO: 4
QSLLYSNGNT Y CDR2 of light chain variable domain
                                          SEQ ID NO: 5
KLS CDR3 of light chain variable domain
                                          SEQ ID NO: 6
SQSTHVPWT heavy chain variable domain of huCD45R0_v3
                                          SEQ ID NO: 7
QITLKESGPT LVKPTQTLTL TCTFSGFSLT TYGIGVGWIR

QPPGKALEWL THIWWNDNKY YSPSLKSRLT ITKDSSKNQV

VLTMTNMDPV DTATYYCLYG YTYWGQGTLV TVSA light chain variable domain of huCD45R0_v3
                                          SEQ ID NO: 8
DVVMTQTPLS LPVTLGQPAS ISCRSSQSLL YSNGNTYLHW

YQQRPGQSPR LLIYKLSNRF SGVPDRFSGS GSGTDFTLKI

SRVEAEDVGV YYCSQSTHVP WTFGGGTKLE IK heavy chain variable domain of huCD45R0_v1
                                          SEQ ID NO: 9
EVQLVESGGG LVQPGGSLRL SCAFSGFSLT TYGIGVGWIR

QAPGKGLEWL THIWWNDNKY YADSVKGRFT ISKDSSKNTV

YLQMNSLRAE DTAVYYCLYG YTYWGQGTLV TVSS light chain variable domain of huCD45R0_v1
                                          SEQ ID NO: 10
DIQMTQSPSS LSASVGDRVT ITCRSSQSLL YSNGNTYLHW

YQQKPGKAPK LLIYKLSNRF SGVPSRFSGS RSGTDFTLTI

SSLQPEDFAT YYCSQSTHVP WTFGQGTKVE IK heavy chain variable domain of huCD45R0_v2
                                          SEQ ID NO: 11
QIQLVESGGG LVQPGGSLRL SCAFSGFSLT TYGIGVGWIR

QAPGKGLEWL THIWWNDNKY YADSVRGRFT ISKDSSKNTV

YLQMNSLRAE DTAVYYCLYG YTYWGQGTLV TVSS
```

Sequence listing light chain variable domain of huCD45R0_v2
SEQ ID NO: 12
DVVMTQTPSS LSASVGDRVT ISCRSSQSLL YSNGNTYLHW
YQQKPGKAPK LLIYKLSNRF SGVPDRFSGS GSGTDFTLTI
SSLQPEDFAT YYCSQSTHVP WTFGQGTKVE IK heavy chain variable domain of muCD45R0
SEQ ID NO: 13
QITLKESGPG ILQPSQTLSL TCSFSGFSLT TYGIGVGWIR
QPPGKGLEWL THIWWNDNKY YNTALRSRLT ISKDSSNNQV
LLKIANVDTA DTATYYCLYG YTYWGQGTLV TVSA light chain variable domain of muCD45R0
SEQ ID NO: 14
DVVMTQTPLS LPVSLGDQAS ISCRSSQSLL YSNGNTYLHW
YLQKPGQSPK LLIYKLSNRF SGVPDRFSGS GSGTDFTLKI
SRVEAEDLGV YFCSQSTHVP WTFGGGTKLE IK heavy chain variable domain of huCD45R0_v4
SEQ ID NO: 15
VQLVESGGGL VQPGGSLRLS CAASGFSLTT YGIGIHWVRQ
APGKGLEWVA RIWWNDNKRY ADSVKGRFTI SADTSKNTAY
LQMNSLRAED TAVYYCLYGY TYWGQGTLVT VSS light chain variable domain of huCD45R0_v4
SEQ ID NO: 16
DIQMTQSPSS LSASVGDRVT ITCRASQSLL YSNGNTYVAW
YQQKPGKAPK LLIYKLSFLY SGVPSRFSGS RSGTDFTLTI
SSLQPEDFAT YYCSQSTHVP WTFGQGTKVE IK heavy chain variable domain of huCD45R0_v5
SEQ ID NO: 17
QITLKESGPT LVKPTQTLTL TCTFSGFSLT TYGIGVGWIR
QPPGKALEWL ALIWWNDNKR YSPSLKSRLT ITKDTSKNQV
VLTMTNMDPV DTATYYCLYG YTYWGQGTLV TVSA light chain variable domain of huCD45R0_v5
SEQ ID NO: 18
DVVMTQSPLS LPVTLGQPAS ISCRSSQSLL YSNGNTYLNW
FQQRPGQSPR RLIYKLSNRD SGVPDRFSGS GSGTDFTLKI
SRVEAEDVGV YYCSQSTHVP WTFGGGTKLE IK humanized anti-P185-Her2 antibody 4d5 heavy
chain variable domain
SEQ ID NO: 19
EVQLVESGGG LVQPGGSLRL SCAASGFNIK DTYIHWVRQA
PGKGLEWVAR IYPTNGYTRY ADSVKGRFTI SADTSKNTAY
LQMNSLRAED TAVYYCSRWG DGFYAMDYW GQGTLVTVSS humanized anti-P185-Her2 antibody 4d5 light
chain variable domain
SEQ ID NO: 20
DIQMTQSPSS LSASVGDRVT ITCRASQDVN TAVAWYQQKP
GKAPKLLIYS ASFLYSGVPS RFSGSRSGTD FTLTISSLQP
EDFATYYCQQ HYTTPPTFGQ GTKVEIK human IgG1 heavy chain constant region CH1
SEQ ID NO: 21
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSC human kappa light chain constant region
SEQ ID NO: 22
RTVAAPSVFI FPPSDEQLKS GTASVVCLLN NFYPREAKVQ
WKVDNALQSG NSQESVTEQD SKDSTYSLSS TLTLSKADYE
KHKVYACEVT HQGLSSPVTK SFNRGEC protein sequence of IGHV2-5*01 allele
according to IMGT®
SEQ ID NO: 23
QITLKESGPT LVKPTQTLTL TCTFSGFSLS TSGVGVGWIR
QPPGKALEWL ALIYWNDDKR YSPSLKSRLT ITKDTSKNQV
VLTMTNMDPV DTATYYCAHR protein sequence of IGKV2-30*01 allele
according to IMGT®
SEQ ID NO: 24
DVVMTQSPLS LPVTLGQPAS ISCRSSQSLV YSDGNTYLNW
FQQRPGQSPR RLIYKVSNRD SGVPDRFSGS GSGTDFTLKI
SRVEAEDVGV YYCMQGTHWP protein sequence of IGHJ5*02 allele
encoding for FR4 according to IMGT®
SEQ ID NO: 25
NWFDPWGQGT LVTVSS protein sequence of IGKJ4*01 allele
encoding for FR4 according to IMGT®
SEQ ID NO: 26
LTFGGGTKVE IK gr_IGHV2-5*01
SEQ ID NO: 27
QITLKESGPT LVKPTQTLTL TCTFSGFSLT TYGIGVGWIR
QPPGKALEWL ALIWWNDNKR YSPSLKSRLT ITKDTSKNQV
VLTMTNMDPV DTATYYC gr_IGKV2-30*01
SEQ ID NO: 28
DVVMTQSPLS LPVTLGQPAS ISCRSSQSLL YSNGNTYLNW
FQQRPGQSPR RLIYKLSNRD SGVPDRFSGS GSGTDFTLKI
SRVEAEDVGV YYC CD45 antigen (PTPRC), isoform 1 UniProt
entry P08575
SEQ ID NO: 29
MYLWLKLLAF GFAFLDTEVF VTGQSPTPSP TGLTTAKMPS
VPLSSDPLPT HTTAFSPAST FERENDFSET TTSLSPDNTS
TQVSPDSLDN ASAFNTTGVS SVQTPHLPTH ADSQTPSAGT
DTQTFSGSAA NAKLNPTPGS NAISDVPGER STASTFPTDP
VSPLTTTLSL AHHSSAALPA RTSNTTITAN TSDAYLNASE
TTTLSPSGSA VISTTTIATT PSKPTCDEKY ANITVDYLYN
KETKLFTAKL NVENVECGN NTCTNNEVHN LTECKNASVS

ISHNSCTAPD KTLILDVPPG VEKFQLHDCT QVEKADTTIC

LKWKNIETFT CDTQNITYRF QCGNMIFDNK EIKLENLEPE

HEYKCDSEIL YNNHKFTNAS KIIKTDFGSP GEPQIIFCRS

EAAHQGVITW NPPQRSFHNF TLCYIKETEK DCLNLDKNLI

KYDLQNLKPY TKYVLSLHAY IIAKVQRNGS AAMCHFTTKS

APPSQVWNMT VSMTSDNSMH VKCRPPRDRN GPHERYHLEV

EAGNTLVRNE SHKNCDFRVK DLQYSTDYTF KAYFHNGDYP

GEPFILHHST SYNSKALIAF LAFLIIVTSI ALLVVLYKIY

DLHKKRSCNL DEQQELVERD DEKQLMNVEP IHADILLETY

KRKIADEGRL FLAEFQSIPR VFSKFPIKEA RKPFNQNKNR

YVDILPYDYN RVELSEINGD AGSNYINASY IDGFKEPRKY

IAAQGPRDET VDDFWRMIWE QKATVIVMVT RCEEGNRNKC

AEYWPSMEEG TRAFGDVVVK INQHKRCPDY IIQKLNIVNK

KEKATGREVT HIQFTSWPDH GVPEDPHLLL KLRRRVNAFS

NFFSGPIVVH CSAGVGRTGT YIGIDAMLEG LEAENKVDVY

GYVVKLRRQR CLMVQVEAQY ILIHQALVEY NQFGETEVNL

SELHPYLHNM KKRDPPSEPS PLEAEFQRLP SYRSWRTQHI

GNQEENKSKN RNSNVIPYDY NRVPLKHELE MSKESEHDSD

ESSDDDSDSE EPSKYINASF IMSYWKPEVM IAAQGPLKET

IGDFWQMIFQ RKVKVIVMLT ELKHGDQEIC AQYWGEGKQT

YGDIEVDLKD TDKSSTYTLR VFELRHSKRK DSRTVYQYQY

TNWSVEQLPA EPKELISMIQ VVKQKLPQKN SSEGNKHHKS

TPLLIHCRDG SQQTGIFCAL LNLLESAETE EVVDIFQVVK

ALRKARPGMV STFEQYQFLY DVIASTYPAQ NGQVKKNNHQ

EDKIEFDNEV DKVKQDANCV NPLGAPEKLP EAKEQAEGSE

PTSGTEGPEH SVNGPASPAL NQGS

SEQ ID NO: 30
TYYCLYGYTY W

HC_muCD45R0
SEQ ID NO: 31
QITLKESGPG ILQPSQTLSL TCSFSGFSLT TYGIGVGWIR

QPPGKGLEWL THIWWNDNKY YNTALRSRLT ISKDSSNNQV

LLKIANVDTA DTATYYC

LC_muCE145R0
SEQ ID NO: 32
DVVMTQTPLS LPVSLGDQAS ISCRSSQSLL YSNGNTYLHW

YLQKPGQSPK LLIYKLSNRF SGVPDRFSGS GSTDFTLKI

SRVEAEDLGV YFC

What is claimed is:

1. A humanized antibody or fragment thereof specific for the antigen CD45R0, wherein said antibody or fragment thereof comprises a humanized heavy chain variable domain comprising a CDR1 region of SEQ ID NO:1, a CDR2 region of SEQ ID NO:2, and a CDR3 region of SEQ ID NO:3, and a humanized light chain variable domain comprising a CDR1 region of SEQ ID NO:4, a CDR2 region of SEQ ID NO:5, and a CDR3 region of SEQ ID NO:6;
   wherein said humanized heavy chain variable domain has artificial framework regions FR1, FR2, FR3, and FR4, and wherein said humanized light chain variable domain has artificial framework regions FR1, FR2, FR3, and FR4;
   wherein said artificial framework regions FR1, FR2, FR3, and FR4 of said humanized heavy chain variable domain are amino acid sequences having an identity of at least 70% to the artificial heavy chain variable sequence framework regions FR1, FR2, FR3, and FR4 of SEQ ID NO:19, and wherein said artificial framework regions FR1, FR2, FR3, and FR4 of said humanized light chain variable domain are amino acid sequences having an identity of at least 70% to the light chain variable sequence framework regions FR1, FR2, FR3, and FR4 of SEQ ID NO:20;
   and wherein said artificial framework regions FR1, FR2, FR3, and FR4 of said humanized heavy and light chain variable domains are amino acid sequences comprising within the heavy chain variable domain amino acid F at position 25, V at position 39, G at position 40, I at position 42, L at position 53, T at position 54, H at position 55, Y at position 66, K at position 80, S at position 82, and V at position 87; and within the light chain variable domain amino acid S at position 25, L at position 39, H at position 40, N at position 66, R at position 67, and F at position 68 according to the IMGT® nomenclature;
   and wherein said antibodies or fragments thereof bind specifically to CD45R0 with a relative affinity of at least 20% for the CD45R0 antigen when compared to the murine CD45R0 antibody comprising the heavy chain variable domain set forth SEQ ID NO:13 and the light chain variable domain set forth in SEQ ID NO:14.

2. The antibody or fragment thereof according to claim 1, wherein said antibody or fragment thereof comprises within the heavy chain variable domain amino acid Q at position 1, I at position 2, F at position 25, V at position 39, G at position 40, I at position 42, L at position 53, T at position 54, H at position 55, Y at position 66, R at position 72, K at position 80, S at position 82, and V at position 87, and within the light chain variable domain amino acid V at position 2, V at position 3, T at position 7, S at position 22, S at position 25, L at position 39, H at position 40, N at position 66, R at position 67, F at position 68, D at position 74, and G at position 80 according to the IMGT® nomenclature.

3. A humanized antibody or fragment thereof specific for the antigen CD45R0, wherein said antibody or fragment thereof comprises a humanized heavy chain variable domain comprising a CDR1 region of SEQ ID NO:1, a CDR2 region of SEQ ID NO:2, and a CDR3 region of SEQ ID NO:3, and a humanized light chain variable domain comprising a CDR1 region of SEQ ID NO:4, a CDR2 region of SEQ ID NO:5, and a CDR3 region of SEQ ID NO:6;
   wherein said humanized heavy chain variable domain has natural framework regions FR1, FR2, and FR3, and wherein said humanized light chain variable domain has natural framework regions FR1, FR2, FR3;
   wherein said natural framework regions FR1, FR2, FR3, and FR4 of said humanized heavy chain variable domain are amino acid sequences having an identity of at least 70% to the natural heavy chain variable sequence framework regions FR1, FR2, and FR3 encoded by one allele of the IGHV2-5 gene, and wherein said natural framework regions FR1, FR2, and FR3 of said humanized light chain variable domain are amino acid sequences having an identity of at least 70% to the light chain variable sequence framework regions FR1, FR2, and FR3 encoded by one allele of the IGKV2-30 gene; and
   wherein said natural framework regions FR1, FR2, FR3, and FR4 of said humanized light chain variable domain are amino acid sequences comprising within the heavy chain variable domain amino acid T at position 54, amino acid H at position 55, Y at position 66, and S at position 82, and within the light chain variable domain amino acid T at position 7, H at position 40, Y at position 42, L at position 52, and F at position 68 according to the IMGT® nomenclature,
   and wherein said antibodies or fragments thereof bind specifically to CD45R0 with a relative affinity of at least 20% for the CD45R0 antigen when compared to the murine CD45R0 antibody comprising the heavy chain variable domain set forth SEQ ID NO:13 and the light chain variable domain set forth in SEQ ID NO:14.

4. The antibody or fragment thereof according to claim 3, wherein said IGHV2-5 allele is IGHV2-5*01, and wherein said IGKV2-30 allele is IGKV2-30*01.

* * * * *

SEQUENCE LISTING

<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: CDR1 of heavy chain variable domain

<400> SEQUENCE: 1

Gly Phe Ser Leu Thr Thr Tyr Gly Ile Gly
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR2 of heavy chain variable domain

<400> SEQUENCE: 2

Ile Trp Trp Asn Asp Asn Lys
1               5

<210> SEQ ID NO 3
<211> LENGTH: 6
<212> TYPE: PRT
<213> ORGANISM: Artificial Sequence
<220> FEATURE:
<223> OTHER INFORMATION: CDR3 of heavy chain variable domain

```
<400> SEQUENCE: 3

Leu Tyr Gly Tyr Thr Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: CDR1 of light chain variable domain

<400> SEQUENCE: 4

Gln Ser Leu Leu Tyr Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: CDR2 of light chain variable domain

<400> SEQUENCE: 5

Lys Leu Ser
1

<210> SEQ ID NO 6
<211> LENGTH: 9
<212> TYPE: PRT
<213> ORGANISM: Artificial Sequence
<220> FEATURE:
<223> OTHER INFORMATION: CDR3 of light chain variable domain

<400> SEQUENCE: 6

Ser Gln Ser Thr His Val Pro Trp Thr
1               5

<210> SEQ ID NO 7
<211> LENGTH: 114
<212> TYPE: PRT
<213> ORGANISM: Artificial Sequence
<220> FEATURE:
<223> OTHER INFORMATION: heavy chain variable domain of huCD45R0_v3

<400> SEQUENCE: 7

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Ile Gly Val Gly Trp Ile Arg Gln Pro Pro Gly Lys Ala Leu Glu
        35                  40                  45

Trp Leu Thr His Ile Trp Trp Asn Asp Asn Lys Tyr Tyr Ser Pro Ser
    50                  55                  60

Leu Lys Ser Arg Leu Thr Ile Thr Lys Asp Ser Ser Lys Asn Gln Val
65                  70                  75                  80

Val Leu Thr Met Thr Asn Met Asp Pro Val Asp Thr Ala Thr Tyr Tyr
                85                  90                  95

Cys Leu Tyr Gly Tyr Thr Tyr Trp Gly Gln Gly Thr Leu Val Thr Val
            100                 105                 110

Ser Ala

<210> SEQ ID NO 8
```

```
<211> LENGTH: 112
<212> TYPE: PRT
<213> ORGANISM: Artificial Sequence
<220> FEATURE:
<223> OTHER INFORMATION: light chain variable domain of huCD45R0_v3

<400> SEQUENCE: 8

Asp Val Val Met Thr Gln Thr Pro Leu Ser Leu Pro Val Thr Leu Gly
1               5                  10                  15

Gln Pro Ala Ser Ile Ser Cys Arg Ser Gln Ser Leu Leu Tyr Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110

<210> SEQ ID NO 9
<211> LENGTH: 114
<212> TYPE: PRT
<213> ORGANISM: Artificial Sequence
<220> FEATURE:
<223> OTHER INFORMATION: heavy chain variable domain of huCD45R0_v1

<400> SEQUENCE: 9

Glu Val Gln Leu Val Glu Ser Gly Gly Gly Leu Val Gln Pro Gly Gly
1               5                  10                  15

Ser Leu Arg Leu Ser Cys Ala Phe Ser Gly Phe Ser Leu Thr Thr Tyr
            20                  25                  30

Gly Ile Gly Val Gly Trp Ile Arg Gln Ala Pro Gly Lys Gly Leu Glu
        35                  40                  45

Trp Leu Thr His Ile Trp Trp Asn Asp Asn Lys Tyr Tyr Ala Asp Ser
    50                  55                  60

Val Lys Gly Arg Phe Thr Ile Ser Lys Asp Ser Ser Lys Asn Thr Val
65                  70                  75                  80

Tyr Leu Gln Met Asn Ser Leu Arg Ala Glu Asp Thr Ala Val Tyr Tyr
                85                  90                  95

Cys Leu Tyr Gly Tyr Thr Tyr Trp Gly Gln Gly Thr Leu Val Thr Val
            100                 105                 110

Ser Ser

<210> SEQ ID NO 10
<211> LENGTH: 112
<212> TYPE: PRT
<213> ORGANISM: Artificial Sequence
<220> FEATURE:
<223> OTHER INFORMATION: light chain variable domain of huCD45R0_v1

<400> SEQUENCE: 10

Asp Ile Gln Met Thr Gln Ser Pro Ser Ser Leu Ser Ala Ser Val Gly
1               5                  10                  15

Asp Arg Val Thr Ile Thr Cys Arg Ser Ser Gln Ser Leu Leu Tyr Ser
            20                  25                  30

Asn Gly Asn Thr Tyr Leu His Trp Tyr Gln Gln Lys Pro Gly Lys Ala
```

```
                35                  40                  45
Pro Lys Leu Leu Ile Tyr Lys Leu Ser Asn Arg Phe Ser Gly Val Pro
 50                  55                  60

Ser Arg Phe Ser Gly Ser Arg Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Thr His Val Pro Trp Thr Phe Gly Gln Gly Thr Lys Val Glu Ile Lys
                100                 105                 110

<210> SEQ ID NO 11
<211> LENGTH: 114
<212> TYPE: PRT
<213> ORGANISM: Artificial Sequence
<220> FEATURE:
<223> OTHER INFORMATION: heavy chain variable domain of huCD45R0_v2

<400> SEQUENCE: 11

Gln Ile Gln Leu Val Glu Ser Gly Gly Gly Leu Val Gln Pro Gly Gly
  1               5                  10                  15

Ser Leu Arg Leu Ser Cys Ala Phe Ser Gly Phe Ser Leu Thr Thr Tyr
                 20                  25                  30

Gly Ile Gly Val Gly Trp Ile Arg Gln Ala Pro Gly Lys Gly Leu Glu
             35                  40                  45

Trp Leu Thr His Ile Trp Trp Asn Asp Asn Lys Tyr Tyr Ala Asp Ser
 50                  55                  60

Val Arg Gly Arg Phe Thr Ile Ser Lys Asp Ser Ser Lys Asn Thr Val
 65                  70                  75                  80

Tyr Leu Gln Met Asn Ser Leu Arg Ala Glu Asp Thr Ala Val Tyr Tyr
                 85                  90                  95

Cys Leu Tyr Gly Tyr Thr Tyr Trp Gly Gln Gly Thr Leu Val Thr Val
                100                 105                 110

Ser Ser

<210> SEQ ID NO 12
<211> LENGTH: 112
<212> TYPE: PRT
<213> ORGANISM: Artificial Sequence
<220> FEATURE:
<223> OTHER INFORMATION: light chain variable domain of huCD45R0_v2

<400> SEQUENCE: 12

Asp Val Val Met Thr Gln Thr Pro Ser Ser Leu Ser Ala Ser Val Gly
  1               5                  10                  15

Asp Arg Val Thr Ile Ser Cys Arg Ser Ser Gln Ser Leu Leu Tyr Ser
                 20                  25                  30

Asn Gly Asn Thr Tyr Leu His Trp Tyr Gln Gln Lys Pro Gly Lys Ala
             35                  40                  45

Pro Lys Leu Leu Ile Tyr Lys Leu Ser Asn Arg Phe Ser Gly Val Pro
 50                  55                  60

Asp Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Thr His Val Pro Trp Thr Phe Gly Gln Gly Thr Lys Val Glu Ile Lys
                100                 105                 110
```

-continued

<210> SEQ ID NO 13
<211> LENGTH: 114
<212> TYPE: PRT
<213> ORGANISM: Mus musculus
<220> FEATURE:
<223> OTHER INFORMATION: heavy chain variable domain of muCD45R0

<400> SEQUENCE: 13

Gln Ile Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Thr Thr Tyr
            20                  25                  30

Gly Ile Gly Val Gly Trp Ile Arg Gln Pro Pro Gly Lys Gly Leu Glu
        35                  40                  45

Trp Leu Thr His Ile Trp Trp Asn Asp Asn Lys Tyr Tyr Asn Thr Ala
    50                  55                  60

Leu Arg Ser Arg Leu Thr Ile Ser Lys Asp Ser Ser Asn Asn Gln Val
65                  70                  75                  80

Leu Leu Lys Ile Ala Asn Val Asp Thr Ala Asp Thr Ala Thr Tyr Tyr
                85                  90                  95

Cys Leu Tyr Gly Tyr Thr Tyr Trp Gly Gln Gly Thr Leu Val Thr Val
            100                 105                 110

Ser Ala

<210> SEQ ID NO 14
<211> LENGTH: 112
<212> TYPE: PRT
<213> ORGANISM: Mus musculus
<220> FEATURE:
<223> OTHER INFORMATION: light chain variable domain of muCD45R0

<400> SEQUENCE: 14

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Tyr Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Leu Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 15
<211> LENGTH: 113
<212> TYPE: PRT
<213> ORGANISM: Artificial Sequence
<220> FEATURE:
<223> OTHER INFORMATION: heavy chain variable domain of huCD45R0_v4

<400> SEQUENCE: 15

Val Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Thr Thr Tyr Gly
            20                  25                  30

```
Ile Gly Ile His Trp Val Arg Gln Ala Pro Gly Lys Gly Leu Glu Trp
            35                  40                  45

Val Ala Arg Ile Trp Trp Asn Asp Asn Lys Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Leu Tyr Gly Tyr Thr Tyr Trp Gly Gln Gly Thr Leu Val Thr Val Ser
            100                 105                 110

Ser
```

<210> SEQ ID NO 16
<211> LENGTH: 112
<212> TYPE: PRT
<213> ORGANISM: Artificial Sequence
<220> FEATURE:
<223> OTHER INFORMATION: light chain variable domain of huCD45R0_v4

<400> SEQUENCE: 16

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Leu Leu Tyr Ser
                20                  25                  30

Asn Gly Asn Thr Tyr Val Ala Trp Tyr Gln Gln Lys Pro Gly Lys Ala
            35                  40                  45

Pro Lys Leu Leu Ile Tyr Lys Leu Ser Phe Leu Tyr Ser Gly Val Pro
 50                  55                  60

Ser Arg Phe Ser Gly Ser Arg Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Thr His Val Pro Trp Thr Phe Gly Gln Gly Thr Lys Val Glu Ile Lys
            100                 105                 110
```

<210> SEQ ID NO 17
<211> LENGTH: 114
<212> TYPE: PRT
<213> ORGANISM: Artificial Sequence
<220> FEATURE:
<223> OTHER INFORMATION: heavy chain variable domain of huCD45R0_v5

<400> SEQUENCE: 17

```
Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Thr Thr Tyr
                20                  25                  30

Gly Ile Gly Val Gly Trp Ile Arg Gln Pro Pro Gly Lys Ala Leu Glu
            35                  40                  45

Trp Leu Ala Leu Ile Trp Trp Asn Asp Asn Lys Arg Tyr Ser Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Leu Tyr Gly Tyr Thr Tyr Trp Gly Gln Gly Thr Leu Val Thr Val
            100                 105                 110
```

Ser Ala

<210> SEQ ID NO 18
<211> LENGTH: 112
<212> TYPE: PRT
<213> ORGANISM: Artificial Sequence
<220> FEATURE:
<223> OTHER INFORMATION: light chain variable domain of huCD45R0_v5

<400> SEQUENCE: 18

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asn Gly Asn Thr Tyr Leu Asn Trp Phe Gln Gln Arg Pro Gly Gln Ser
        35                  40                  45

Pro Arg Arg Leu Ile Tyr Lys Leu Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Leu Glu Ile Lys
            100                 105                 110
```

<210> SEQ ID NO 19
<211> LENGTH: 120
<212> TYPE: PRT
<213> ORGANISM: Artificial Sequence
<220> FEATURE:
<223> OTHER INFORMATION: humanized anti-P185-Her2 antibody 4d5 heavy
      chain variable

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 20
<211> LENGTH: 107
<212> TYPE: PRT
<213> ORGANISM: Artificial Sequence
<220> FEATURE:
<223> OTHER INFORMATION: humanized anti-P185-Her2 antibody 4d5 light
      chain variable

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 21
<211> LENGTH: 103
<212> TYPE: PRT
<213> ORGANISM: Homo sapiens
<220> FEATURE:
<223> OTHER INFORMATION: human IgG1 heavy chain constant region CH1

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 22
<211> LENGTH: 107
<212> TYPE: PRT
<213> ORGANISM: Homo sapiens
<220> FEATURE:
<223> OTHER INFORMATION: human kappa light chain constant region

<400> SEQUENCE: 22

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105

<210> SEQ ID NO 23
<211> LENGTH: 100
<212> TYPE: PRT
<213> ORGANISM: Homo sapiens
<220> FEATURE:
<223> OTHER INFORMATION: protein sequence of IGHV2-5*01 allele
      according to IMGT

<400> SEQUENCE: 23

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100

<210> SEQ ID NO 24
<211> LENGTH: 100
<212> TYPE: PRT
<213> ORGANISM: Homo sapiens
<220> FEATURE:
<223> OTHER INFORMATION: protein sequence of IGKV2-30*01 allele
      according to IMGT

<400> SEQUENCE: 24

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 25
<211> LENGTH: 16
<212> TYPE: PRT
<213> ORGANISM: Homo sapiens
<220> FEATURE:
<223> OTHER INFORMATION: protein sequence of IGHJ5*02 allele encoding
      for FR4 according to IMGT

<400> SEQUENCE: 25
```

```
Asn Trp Phe Asp Pro Trp Gly Gln Gly Thr Leu Val Thr Val Ser Ser
1               5                   10                  15
```

<210> SEQ ID NO 26
<211> LENGTH: 12
<212> TYPE: PRT
<213> ORGANISM: Homo sapiens
<220> FEATURE:
<223> OTHER INFORMATION: protein sequence of IGKJ4*01 allele encoding
      for FR4 according to IMGT

<400> SEQUENCE: 26

```
Leu Thr Phe Gly Gly Gly Thr Lys Val Glu Ile Lys
1               5                   10
```

<210> SEQ ID NO 27
<211> LENGTH: 97
<212> TYPE: PRT
<213> ORGANISM: Artificial Sequence
<220> FEATURE:
<223> OTHER INFORMATION: gr_IGHV2-5*01

<400> SEQUENCE: 27

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Thr Tyr
                20                  25                  30

Gly Ile Gly Val Gly Trp Ile Arg Gln Pro Pro Gly Lys Ala Leu Glu
            35                  40                  45

Trp Leu Ala Leu Ile Trp Trp Asn Asp Asn Lys Arg Tyr Ser Pro Ser
50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys
```

<210> SEQ ID NO 28
<211> LENGTH: 93
<212> TYPE: PRT
<213> ORGANISM: Artificial Sequence
<220> FEATURE:
<223> OTHER INFORMATION: gr_IGKV2-30*01

<400> SEQUENCE: 28

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
                20                  25                  30

Asn Gly Asn Thr Tyr Leu Asn Trp Phe Gln Gln Arg Pro Gly Gln Ser
            35                  40                  45

Pro Arg Arg Leu Ile Tyr Lys Leu Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys
                85                  90
```

<210> SEQ ID NO 29
<211> LENGTH: 1304
<212> TYPE: PRT

<213> ORGANISM: Homo sapiens
<220> FEATURE:
<223> OTHER INFORMATION: CD45 antigen (PTPRC), isoform 1

<400> SEQUENCE: 29

```
Met Tyr Leu Trp Leu Lys Leu Leu Ala Phe Gly Phe Ala Phe Leu Asp
1               5                   10                  15

Thr Glu Val Phe Val Thr Gly Gln Ser Pro Thr Pro Ser Pro Thr Gly
            20                  25                  30

Leu Thr Thr Ala Lys Met Pro Ser Val Pro Leu Ser Ser Asp Pro Leu
        35                  40                  45

Pro Thr His Thr Thr Ala Phe Ser Pro Ala Ser Thr Phe Glu Arg Glu
    50                  55                  60

Asn Asp Phe Ser Glu Thr Thr Thr Ser Leu Ser Pro Asp Asn Thr Ser
65                  70                  75                  80

Thr Gln Val Ser Pro Asp Ser Leu Asp Asn Ala Ser Ala Phe Asn Thr
                85                  90                  95

Thr Gly Val Ser Ser Val Gln Thr Pro His Leu Pro Thr His Ala Asp
            100                 105                 110

Ser Gln Thr Pro Ser Ala Gly Thr Asp Thr Gln Thr Phe Ser Gly Ser
        115                 120                 125

Ala Ala Asn Ala Lys Leu Asn Pro Thr Pro Gly Ser Asn Ala Ile Ser
130                 135                 140

Asp Val Pro Gly Glu Arg Ser Thr Ala Ser Thr Phe Pro Thr Asp Pro
145                 150                 155                 160

Val Ser Pro Leu Thr Thr Thr Leu Ser Leu Ala His His Ser Ser Ala
                165                 170                 175

Ala Leu Pro Ala Arg Thr Ser Asn Thr Thr Ile Thr Ala Asn Thr Ser
            180                 185                 190

Asp Ala Tyr Leu Asn Ala Ser Glu Thr Thr Thr Leu Ser Pro Ser Gly
        195                 200                 205

Ser Ala Val Ile Ser Thr Thr Thr Ile Ala Thr Thr Pro Ser Lys Pro
210                 215                 220

Thr Cys Asp Glu Lys Tyr Ala Asn Ile Thr Val Asp Tyr Leu Tyr Asn
225                 230                 235                 240

Lys Glu Thr Lys Leu Phe Thr Ala Lys Leu Asn Val Asn Glu Asn Val
                245                 250                 255

Glu Cys Gly Asn Asn Thr Cys Thr Asn Asn Glu Val His Asn Leu Thr
            260                 265                 270

Glu Cys Lys Asn Ala Ser Val Ser Ile Ser His Asn Ser Cys Thr Ala
        275                 280                 285

Pro Asp Lys Thr Leu Ile Leu Asp Val Pro Pro Gly Val Glu Lys Phe
290                 295                 300

Gln Leu His Asp Cys Thr Gln Val Glu Lys Ala Asp Thr Thr Ile Cys
305                 310                 315                 320

Leu Lys Trp Lys Asn Ile Glu Thr Phe Thr Cys Asp Thr Gln Asn Ile
                325                 330                 335

Thr Tyr Arg Phe Gln Cys Gly Asn Met Ile Phe Asp Asn Lys Glu Ile
            340                 345                 350

Lys Leu Glu Asn Leu Glu Pro Glu His Glu Tyr Lys Cys Asp Ser Glu
        355                 360                 365

Ile Leu Tyr Asn Asn His Lys Phe Thr Asn Ala Ser Lys Ile Ile Lys
370                 375                 380

Thr Asp Phe Gly Ser Pro Gly Glu Pro Gln Ile Ile Phe Cys Arg Ser
```

```
            385                 390                 395                 400
        Glu Ala Ala His Gln Gly Val Ile Thr Trp Asn Pro Pro Gln Arg Ser
                        405                 410                 415

Phe His Asn Phe Thr Leu Cys Tyr Ile Lys Glu Thr Glu Lys Asp Cys
                        420                 425                 430

Leu Asn Leu Asp Lys Asn Leu Ile Lys Tyr Asp Leu Gln Asn Leu Lys
                        435                 440                 445

Pro Tyr Thr Lys Tyr Val Leu Ser Leu His Ala Tyr Ile Ile Ala Lys
                        450                 455                 460

Val Gln Arg Asn Gly Ser Ala Ala Met Cys His Phe Thr Thr Lys Ser
        465                 470                 475                 480

Ala Pro Pro Ser Gln Val Trp Asn Met Thr Val Ser Met Thr Ser Asp
                        485                 490                 495

Asn Ser Met His Val Lys Cys Arg Pro Arg Asp Arg Asn Gly Pro
                        500                 505                 510

His Glu Arg Tyr His Leu Glu Val Glu Ala Gly Asn Thr Leu Val Arg
                        515                 520                 525

Asn Glu Ser His Lys Asn Cys Asp Phe Arg Val Lys Asp Leu Gln Tyr
                        530                 535                 540

Ser Thr Asp Tyr Thr Phe Lys Ala Tyr Phe His Asn Gly Asp Tyr Pro
        545                 550                 555                 560

Gly Glu Pro Phe Ile Leu His His Ser Thr Ser Tyr Asn Ser Lys Ala
                        565                 570                 575

Leu Ile Ala Phe Leu Ala Phe Leu Ile Ile Val Thr Ser Ile Ala Leu
                        580                 585                 590

Leu Val Val Leu Tyr Lys Ile Tyr Asp Leu His Lys Lys Arg Ser Cys
                        595                 600                 605

Asn Leu Asp Glu Gln Gln Glu Leu Val Glu Arg Asp Asp Glu Lys Gln
                        610                 615                 620

Leu Met Asn Val Glu Pro Ile His Ala Asp Ile Leu Leu Glu Thr Tyr
        625                 630                 635                 640

Lys Arg Lys Ile Ala Asp Glu Gly Arg Leu Phe Leu Ala Glu Phe Gln
                        645                 650                 655

Ser Ile Pro Arg Val Phe Ser Lys Phe Pro Ile Lys Glu Ala Arg Lys
                        660                 665                 670

Pro Phe Asn Gln Asn Lys Asn Arg Tyr Val Asp Ile Leu Pro Tyr Asp
                        675                 680                 685

Tyr Asn Arg Val Glu Leu Ser Glu Ile Asn Gly Asp Ala Gly Ser Asn
                        690                 695                 700

Tyr Ile Asn Ala Ser Tyr Ile Asp Gly Phe Lys Glu Pro Arg Lys Tyr
        705                 710                 715                 720

Ile Ala Ala Gln Gly Pro Arg Asp Glu Thr Val Asp Asp Phe Trp Arg
                        725                 730                 735

Met Ile Trp Glu Gln Lys Ala Thr Val Ile Val Met Val Thr Arg Cys
                        740                 745                 750

Glu Glu Gly Asn Arg Asn Lys Cys Ala Glu Tyr Trp Pro Ser Met Glu
                        755                 760                 765

Glu Gly Thr Arg Ala Phe Gly Asp Val Val Lys Ile Asn Gln His
                        770                 775                 780

Lys Arg Cys Pro Asp Tyr Ile Ile Gln Lys Leu Asn Ile Val Asn Lys
        785                 790                 795                 800

Lys Glu Lys Ala Thr Gly Arg Glu Val Thr His Ile Gln Phe Thr Ser
                        805                 810                 815
```

```
Trp Pro Asp His Gly Val Pro Glu Asp Pro His Leu Leu Lys Leu
            820                 825                 830

Arg Arg Arg Val Asn Ala Phe Ser Asn Phe Phe Ser Gly Pro Ile Val
            835                 840                 845

Val His Cys Ser Ala Gly Val Gly Arg Thr Gly Thr Tyr Ile Gly Ile
            850                 855                 860

Asp Ala Met Leu Glu Gly Leu Glu Ala Glu Asn Lys Val Asp Val Tyr
865                 870                 875                 880

Gly Tyr Val Val Lys Leu Arg Arg Gln Arg Cys Leu Met Val Gln Val
                885                 890                 895

Glu Ala Gln Tyr Ile Leu Ile His Gln Ala Leu Val Glu Tyr Asn Gln
            900                 905                 910

Phe Gly Glu Thr Glu Val Asn Leu Ser Glu Leu His Pro Tyr Leu His
            915                 920                 925

Asn Met Lys Lys Arg Asp Pro Pro Ser Glu Pro Ser Pro Leu Glu Ala
930                 935                 940

Glu Phe Gln Arg Leu Pro Ser Tyr Arg Ser Trp Arg Thr Gln His Ile
945                 950                 955                 960

Gly Asn Gln Glu Glu Asn Lys Ser Lys Asn Arg Asn Ser Asn Val Ile
            965                 970                 975

Pro Tyr Asp Tyr Asn Arg Val Pro Leu Lys His Glu Leu Glu Met Ser
            980                 985                 990

Lys Glu Ser Glu His Asp Ser Asp Glu Ser Ser Asp Asp Ser Asp
            995                 1000                1005

Ser Glu Glu Pro Ser Lys Tyr Ile Asn Ala Ser Phe Ile Met Ser Tyr
    1010                1015                1020

Trp Lys Pro Glu Val Met Ile Ala Ala Gln Gly Pro Leu Lys Glu Thr
1025                1030                1035                1040

Ile Gly Asp Phe Trp Gln Met Ile Phe Gln Arg Lys Val Lys Val Ile
            1045                1050                1055

Val Met Leu Thr Glu Leu Lys His Gly Asp Gln Glu Ile Cys Ala Gln
            1060                1065                1070

Tyr Trp Gly Glu Gly Lys Gln Thr Tyr Gly Asp Ile Glu Val Asp Leu
            1075                1080                1085

Lys Asp Thr Asp Lys Ser Ser Thr Tyr Thr Leu Arg Val Phe Glu Leu
    1090                1095                1100

Arg His Ser Lys Arg Lys Asp Ser Arg Thr Val Tyr Gln Tyr Gln Tyr
1105                1110                1115                1120

Thr Asn Trp Ser Val Glu Gln Leu Pro Ala Glu Pro Lys Glu Leu Ile
            1125                1130                1135

Ser Met Ile Gln Val Val Lys Gln Lys Leu Pro Gln Lys Asn Ser Ser
            1140                1145                1150

Glu Gly Asn Lys His His Lys Ser Thr Pro Leu Leu Ile His Cys Arg
            1155                1160                1165

Asp Gly Ser Gln Gln Thr Gly Ile Phe Cys Ala Leu Leu Asn Leu Leu
            1170                1175                1180

Glu Ser Ala Glu Thr Glu Glu Val Val Asp Ile Phe Gln Val Val Lys
1185                1190                1195                1200

Ala Leu Arg Lys Ala Arg Pro Gly Met Val Ser Thr Phe Glu Gln Tyr
            1205                1210                1215

Gln Phe Leu Tyr Asp Val Ile Ala Ser Thr Tyr Pro Ala Gln Asn Gly
            1220                1225                1230
```

-continued

```
Gln Val Lys Lys Asn Asn His Gln Glu Asp Lys Ile Glu Phe Asp Asn
        1235                1240                1245

Glu Val Asp Lys Val Lys Gln Asp Ala Asn Cys Val Asn Pro Leu Gly
        1250                1255                1260

Ala Pro Glu Lys Leu Pro Glu Ala Lys Glu Gln Ala Glu Gly Ser Glu
1265                1270                1275                1280

Pro Thr Ser Gly Thr Glu Gly Pro Glu His Ser Val Asn Gly Pro Ala
                1285                1290                1295

Ser Pro Ala Leu Asn Gln Gly Ser
            1300
```